US012678540B2

(12) United States Patent
Wei et al.

(10) Patent No.: US 12,678,540 B2
(45) Date of Patent: Jul. 14, 2026

(54) CHIMERIC PEPTIDE-MODIFIED SIS MEMBRANE, PREPARATION METHOD THEREFOR AND APPLICATION THEREOF

(71) Applicant: Beijing Biosis Healing Biological Technology Co., Ltd., Beijing (CN)

(72) Inventors: Pengfei Wei, Beijing (CN); Huasheng Wang, Beijing (CN); Bo Zhao, Beijing (CN)

(73) Assignee: Beijing Biosis Healing Biological Technology Co., Ltd., Beijing (CN)

( * ) Notice: Subject to any disclaimer, the term of this patent is extended or adjusted under 35 U.S.C. 154(b) by 469 days.

(21) Appl. No.: 18/557,084

(22) PCT Filed: Jun. 2, 2021

(86) PCT No.: PCT/CN2021/097851
§ 371 (c)(1),
(2) Date: Oct. 25, 2023

(87) PCT Pub. No.: WO2022/227225
PCT Pub. Date: Nov. 3, 2022

(65) Prior Publication Data

US 2024/0424167 A1 Dec. 26, 2024

(30) Foreign Application Priority Data

Apr. 27, 2021 (CN) ......................... 202110459709.8

(51) Int. Cl.
*A61L 27/00* (2006.01)
*A61L 27/22* (2006.01)
*A61L 27/36* (2006.01)
*A61L 27/54* (2006.01)
*C07K 14/00* (2006.01)

(52) U.S. Cl.
CPC ......... *A61L 27/3629* (2013.01); *A61L 27/227* (2013.01); *A61L 27/54* (2013.01); *C07K 14/001* (2013.01)

(58) Field of Classification Search
CPC ............... A61L 27/3629; A61L 27/227; A61L 2430/02; C07K 14/4723; C07K 14/78; C07K 19/00; C07K 2319/33
See application file for complete search history.

(56) References Cited

U.S. PATENT DOCUMENTS 5,912,230 A 6/1999 Oppenheim et al.
2013/0345118 A1 12/2013 Rolle et al.
2017/0305984 A1 10/2017 Siqueria et al.

FOREIGN PATENT DOCUMENTS

CN 105859841 A 8/2016
CN 110022907 A 7/2019

(Continued)

OTHER PUBLICATIONS

Lozeau et al. (Acta Biommateriala. vol. 52, Apr. 1, 2017, pp. 9-20.*
Melino et al. (FEBS Journal, vol. 281, Dec. 2014).*
Yang (Chinese Journal of Reparative and Reconstructive Surgery. vol. 27, No. 9, Aug. 2013.*
Zihao Liu et al., *Histatin 1-modified SIS hydrogels enhance the sealing of peri-implant mucosa to prevent peri-implantitis*; iScience 26, 108212, Nov. 17, 2023.

(Continued)

*Primary Examiner* — Jeanette M Lieb
(74) *Attorney, Agent, or Firm* — The Dobrusin Law Firm, P.C.

(57) ABSTRACT

A chimeric peptide-modified SIS membrane, a preparation method therefor and an application thereof. The chimeric peptide-modified SIS membrane is used to promote the expression of ITG-α3, ITG-β1, BMP2, RUNX2, ALP and OPN, and inhibits the growth of *Streptococcus gordonii* and *Streptococcus sanguinis*, thereby enabling the SIS membrane to exert antibacterial, osteogenic and healing-promoting biological functions. The SIS membrane (that is, a chimeric peptide-modified GBR film) can be used for clinical treatment of infectious bone defects.

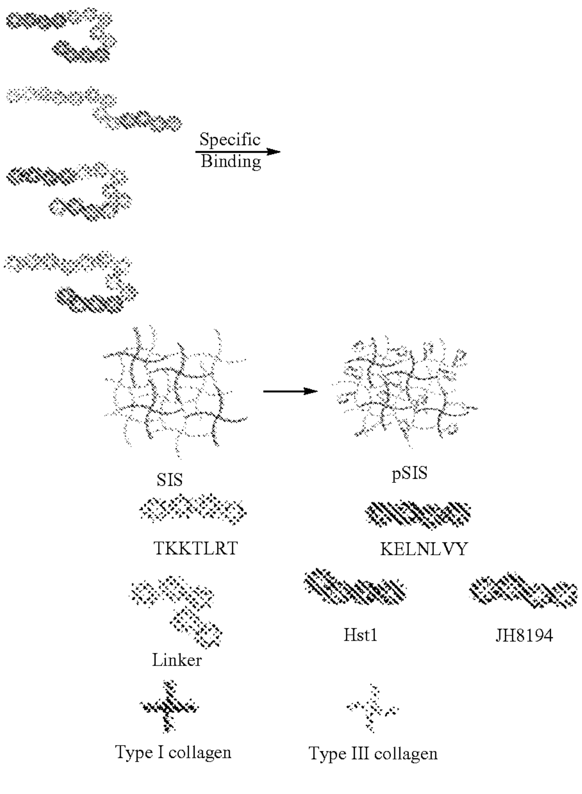

15 Claims, 12 Drawing Sheets

Specification includes a Sequence Listing.

(56) References Cited

FOREIGN PATENT DOCUMENTS

| | | | | | |
|---|---|---|---|---|---|
| CN | 111050778 | A | * | 4/2020 | ............ A61K 47/64 |
| CN | 112410316 | A | | 2/2021 | |
| WO | 2015061331 | A1 | | 4/2015 | |
| WO | 2019/075213 | A1 | | 4/2019 | |

OTHER PUBLICATIONS

Yuanyuan Zheng et al., *Injectable supramolecular gelatin hydrogel loading of resveratrol and histatin-1 for burn wound therapy*, Biomater. Sci., 2020, 8, 4810.

Guangxiu Cao et al., *Small intestinal submucosa superiority, limitations and solutions, and its potential to address bottlenecks in tissue repair*; J. Mater. Chem. B, 2019, 7, 5038.

International Search Report and Written Opinion dated Jan. 26, 2022, for International Application PCT/CN2021/097851.

Mu, Yuzhu et al., "Multifunctional Modification of SIS Membrane with Chimeric Peptides to Promote Its Antibacterial. Osteogenic. and Healing-Promoting Abilities for Applying to GBR" Adv. Funct. Mater., vol. 31. May 28, 2021 (May 28, 2021). article No. 2101452. pp. 1-14.

Lozeau, L. D. et al., "Collagen tethering of synthetic human antimicrobial peptides cathelicidin LL37 and its effects on antimicrobial activity and cytotoxicity" Acta Biomaterialia, vol. 52. Dec. 23, 2016 (Dec. 23, 2016). pp. 9-20.

Yang, Kai et al., Recent Progress of Small Intestinal Submucosa in Application Research of Tissue Repair and Reconstruction (Chinese Journal of Reparative and Reconstructive Surgery), vol. 27. No. 9. Aug. 15, 2013 (Aug. 15, 2013). pp. 1138-1143.

Melino, S. et al., "Histatins: salivary peptides with copper (II)-and zinc(II)-binding motifs Perspectives for biomedical applications" FEES Journal, vol. vol. 281, Dec. 31, 2014 (Dec. 31, 2014), pp. 657-672.

* cited by examiner

SEQUENCE LISTING

```
<160> NUMBER OF SEQ ID NOS: 32

<210> SEQ ID NO 1
<211> LENGTH: 29
<212> TYPE: PRT
<213> ORGANISM: Artificial Sequence
<220> FEATURE:
<223> OTHER INFORMATION: sequence of the chimeric peptide

<400> SEQUENCE: 1

Thr Lys Lys Thr Leu Arg Thr Gly Gly Gly Gly Ser Gly Gly Gly Gly
```

-continued 1 5 10 15

Ser Lys Phe His Glu Lys His His Ser His Arg Gly Tyr
20 25

<210> SEQ ID NO 2
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 2

Thr Lys Lys Thr Leu Arg Thr Gly Gly Gly Gly Ser Gly Gly Gly Gly
1 5 10 15

Ser Lys Arg Leu Phe Arg Arg Leu Leu Phe Ser Met Lys Lys Tyr
20 25 30

<210> SEQ ID NO 3
<211> LENGTH: 29
<212> TYPE: PRT
<213> ORGANISM: Artificial Sequence
<220> FEATURE:
<223> OTHER INFORMATION: sequence of the chimeric peptide

<400> SEQUENCE: 3

Lys Glu Leu Asn Leu Val Tyr Gly Gly Gly Gly Ser Gly Gly Gly Gly
1 5 10 15

Ser Lys Phe His Glu Lys His His Ser His Arg Gly Tyr
20 25

<210> SEQ ID NO 4
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 4

Lys Glu Leu Asn Leu Val Tyr Gly Gly Gly Gly Ser Gly Gly Gly Gly
1 5 10 15

Ser Lys Arg Leu Phe Arg Arg Leu Leu Phe Ser Met Lys Lys Tyr
20 25 30

<210> SEQ ID NO 5
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 5

Thr Lys Lys Thr Leu Arg Thr Gly Gly Gly Gly Ser Gly Gly Gly Gly
1 5 10 15

Ser Arg Lys Phe His Glu Lys His His Ser His Arg Gly Tyr
20 25 30

<210> SEQ ID NO 6
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 6

-continued

Thr Lys Lys Thr Leu Arg Thr Gly Gly Gly Gly Ser Gly Gly Gly Gly
1 5 10 15

Ser Phe Lys Cys Lys Lys Val Val Ile Ser Leu Arg Arg Tyr
20 25 30

<210> SEQ ID NO 7
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 7

Lys Glu Leu Asn Leu Val Tyr Gly Gly Gly Gly Ser Gly Gly Gly Gly
1 5 10 15

Ser Arg Lys Phe His Glu Lys His His Ser His Arg Gly Tyr
20 25 30

<210> SEQ ID NO 8
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 8

Lys Glu Leu Asn Leu Val Tyr Gly Gly Gly Gly Ser Gly Gly Gly Gly
1 5 10 15

Ser Phe Lys Cys Lys Lys Val Val Ile Ser Leu Arg Arg Tyr
20 25 30

<210> SEQ ID NO 9
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 9

Thr Lys Lys Thr Leu Arg Thr Gly Gly Gly Gly Ser Gly Gly Gly Gly
1 5 10 15

Ser Ser His Arg Glu Phe Pro Phe Tyr Gly Asp Tyr Gly Ser
20 25 30

<210> SEQ ID NO 10
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 10

Thr Lys Lys Thr Leu Arg Thr Gly Gly Gly Gly Ser Gly Gly Gly Gly
1 5 10 15

Ser Lys Arg Leu Phe Arg Arg Trp Gln Trp Arg Met Lys Lys Tyr
20 25 30

<210> SEQ ID NO 11
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 11

-continued

Lys Glu Leu Asn Leu Val Tyr Gly Gly Gly Gly Ser Gly Gly Gly Gly
1 5 10 15

Ser Ser His Arg Glu Phe Pro Phe Tyr Gly Asp Tyr Gly Ser
20 25 30

<210> SEQ ID NO 12
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 12

Lys Glu Leu Asn Leu Val Tyr Gly Gly Gly Gly Ser Gly Gly Gly Gly
1 5 10 15

Ser Lys Arg Leu Phe Arg Arg Trp Gln Trp Arg Met Lys Lys Tyr
20 25 30

<210> SEQ ID NO 13
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 13

Thr Lys Lys Thr Leu Arg Thr Glu Ala Ala Ala Lys Glu Ala Ala Ala
1 5 10 15

Lys Ser His Arg Glu Phe Pro Phe Tyr Gly Asp Tyr Gly Ser
20 25 30

<210> SEQ ID NO 14
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 14

Thr Lys Lys Thr Leu Arg Thr Glu Ala Ala Ala Lys Glu Ala Ala Ala
1 5 10 15

Lys Lys Arg Leu Phe Arg Arg Trp Gln Trp Arg Met Lys Lys Tyr
20 25 30

<210> SEQ ID NO 15
<211> LENGTH: 30
<212> TYPE: PRT
<213> ORGANISM: Artificial Sequence
<220> FEATURE:
<223> OTHER INFORMATION: sequence of the chimeric peptide

<400> SEQUENCE: 15

Lys Glu Leu Asn Leu Val Tyr Glu Ala Ala Ala Lys Glu Ala Ala Ala
1 5 10 15

Lys Ser His Arg Glu Phe Pro Phe Tyr Gly Asp Tyr Gly Ser
20 25 30

<210> SEQ ID NO 16
<211> LENGTH: 31
<212> TYPE: PRT
<213> ORGANISM: Artificial Sequence
<220> FEATURE:
<223> OTHER INFORMATION: sequence of the chimeric peptide

<400> SEQUENCE: 16

Lys Glu Leu Asn Leu Val Tyr Glu Ala Ala Ala Lys Glu Ala Ala Ala
1 5 10 15

Lys Lys Arg Leu Phe Arg Arg Trp Gln Trp Arg Met Lys Lys Tyr
20 25 30

<210> SEQ ID NO 17
<211> LENGTH: 19
<212> TYPE: DNA
<213> ORGANISM: Artificial Sequence
<220> FEATURE:
<223> OTHER INFORMATION: Primer Sequence

<400> SEQUENCE: 17
tgcggtctcc taaaggtcg 19

<210> SEQ ID NO 18
<211> LENGTH: 20
<212> TYPE: DNA
<213> ORGANISM: Artificial Sequence
<220> FEATURE:
<223> OTHER INFORMATION: Primer Sequence

<400> SEQUENCE: 18
actcaaactc gctgaggacg 20

<210> SEQ ID NO 19
<211> LENGTH: 20
<212> TYPE: DNA
<213> ORGANISM: Artificial Sequence
<220> FEATURE:
<223> OTHER INFORMATION: Primer Sequence

<400> SEQUENCE: 19
ccgaactggt ccgcaccgac 20

<210> SEQ ID NO 20
<211> LENGTH: 20
<212> TYPE: DNA
<213> ORGANISM: Artificial Sequence
<220> FEATURE:
<223> OTHER INFORMATION: Primer Sequence

<400> SEQUENCE: 20
cttgaaggcc acgggcaggg 20

<210> SEQ ID NO 21
<211> LENGTH: 18
<212> TYPE: DNA
<213> ORGANISM: Artificial Sequence
<220> FEATURE:
<223> OTHER INFORMATION: Primer Sequence

<400> SEQUENCE: 21
aggcaggatt gaccacgg 18

<210> SEQ ID NO 22
<211> LENGTH: 18
<212> TYPE: DNA
<213> ORGANISM: Artificial Sequence
<220> FEATURE:
<223> OTHER INFORMATION: Primer Sequence

<400> SEQUENCE: 22
tgtagttctg ctcatgga 18

<210> SEQ ID NO 23
<211> LENGTH: 17
<212> TYPE: DNA
<213> ORGANISM: Artificial Sequence
<220> FEATURE:
<223> OTHER INFORMATION: Primer Sequence

<400> SEQUENCE: 23
aatgaagggc cctgagc 17

<210> SEQ ID NO 24
<211> LENGTH: 19
<212> TYPE: DNA
<213> ORGANISM: Artificial Sequence
<220> FEATURE:
<223> OTHER INFORMATION: Primer Sequence

<400> SEQUENCE: 24
gccagttctg caaggaagc 19

<210> SEQ ID NO 25
<211> LENGTH: 21
<212> TYPE: DNA
<213> ORGANISM: Artificial Sequence
<220> FEATURE:
<223> OTHER INFORMATION: Primer Sequence

<400> SEQUENCE: 25
gacggccgca tcttcttgtg c 21

<210> SEQ ID NO 26
<211> LENGTH: 21
<212> TYPE: DNA
<213> ORGANISM: Artificial Sequence
<220> FEATURE:
<223> OTHER INFORMATION: Primer Sequence

<400> SEQUENCE: 26
tgcaaatggc agccctggtg a 21

<210> SEQ ID NO 27
<211> LENGTH: 22
<212> TYPE: DNA
<213> ORGANISM: Artificial Sequence
<220> FEATURE:
<223> OTHER INFORMATION: Primer Sequence

<400> SEQUENCE: 27
cctacttctg cacgatgtga tg 22

<210> SEQ ID NO 28
<211> LENGTH: 23
<212> TYPE: DNA
<213> ORGANISM: Artificial Sequence
<220> FEATURE:
<223> OTHER INFORMATION: Primer Sequence

<400> SEQUENCE: 28
cctttgctac ggttggttac att 23

<210> SEQ ID NO 29
<211> LENGTH: 21
<212> TYPE: DNA
<213> ORGANISM: Artificial Sequence
<220> FEATURE:

-continued

```
<223> OTHER INFORMATION: Primer Sequence

<400> SEQUENCE: 29

ctaccacaac gagatgtgca a                                               21


<210> SEQ ID NO 30
<211> LENGTH: 21
<212> TYPE: DNA
<213> ORGANISM: Artificial Sequence
<220> FEATURE:
<223> OTHER INFORMATION: Primer Sequence

<400> SEQUENCE: 30

ccgaagtaca cagtgttctg g                                               21


<210> SEQ ID NO 31
<211> LENGTH: 21
<212> TYPE: DNA
<213> ORGANISM: Artificial Sequence
<220> FEATURE:
<223> OTHER INFORMATION: Primer Sequence

<400> SEQUENCE: 31

ggagcgagat ccctccaaaa t                                               21


<210> SEQ ID NO 32
<211> LENGTH: 23
<212> TYPE: DNA
<213> ORGANISM: Artificial Sequence
<220> FEATURE:
<223> OTHER INFORMATION: Primer Sequence

<400> SEQUENCE: 32

ggctgttgtc atacttctca tgg                                             23
```

CHIMERIC PEPTIDE-MODIFIED SIS MEMBRANE, PREPARATION METHOD THEREFOR AND APPLICATION THEREOF

SEQUENCE LISTING

This application contains a Sequence Listing that has been submitted electronically as an ASCII text file named "Sequence Listing-6733-2143380US_ST25.txt." The ASCII text file, created on May 9, 2024, is 9,490 bytes in size. The material in the ASCII text file is hereby incorporated by reference in its entirety for all purposes.

TECHNICAL FIELD

The present disclosure relates to the field of biomedical materials, specifically to a chimeric peptide-binding SIS membrane and a preparation method and application thereof.

BACKGROUND

Bone defect caused by trauma, tumor, inflammation and other reasons remain as irremediable obstacles in current bone reconstruction. Periodontitis and peri-implantitis are common causes of alveolar bone loss due to plaque biofilm, which can eventually lead to tooth or implant loss and insufficient bone of dental implant area. Guided Bone Regeneration (GBR) technology is considered as one of the methods most commonly applied to reconstruct bone deficiencies. It requires a barrier membrane to prevent the growth of epithelial cells and fibrous connective tissue into defect area, thus ensuring osteoblasts can fill the bone defect space to obtain the desired bone regeneration. The performance of GBR membrane plays an important role in the application of GBR technology, which is closely related to the prevention of bacterial infection, wound healing and bone regeneration after GBR operation.

Extracellular Matrix (ECM) material is a non-cellular biological network composed of collagen (mainly type I and III) and various glycoproteins, which has become a hotspot for tissue engineering scaffold in recent years. Small Intestinal Submucosa (SIS) is the most commonly used ECM material because of its wide sources and easy availability. SIS has many excellent properties, including site-specific tissue regeneration ability, low immunogenicity, excellent mechanical properties, as well as contains multifarious cytokines. It has been used as a scaffold material in many types of tissue and achieved satisfactory results. However, infectious bone defect caused by periodontitis and peri-implantitis and periapical periodontitis is a difficult problem for GBR. Although SIS membrane has excellent mechanical properties and biocompatibility, its capabilities of antibacterial, osteogenesis and healing-promoting are limited. In order to address these limitations, it is desirable to find a suitable way for modification of SIS. Antimicrobial Peptides (AMPs), as an important part of innate immunity, show broad-spectrum, strong and stable antimicrobial activities and good biocompatibility, having become a new generation of potential antibacterial drugs. Histatins (HSTs) are a class of AMPs secreted by human main salivary glands. Due to the cation and weak amphiphilic character, HSTs exhibit a broad-spectrum antibacterial activity in warm and humid oral environment. Hst5 is a major member of HSTs, which can resist LPS of *Porphyromonas gingivalis* (Pg) by IKK/NFκB pathway and inhibit the expression of IL-6 and IL-8 induced by Pg outer membrane protein. Previous study has showed that JH8194, a derivative peptide of Hst5, also has good antibacterial activity which can prevent peri-implantitis and peri-impant mucositis effectively. Except for antibacterial activity, JH8194 also has a certain ability to promote bone formation. It has been found that JH8194 could stimulate the expressions of Runx2, Opn and Alp in MC3T3-E1 while inhibiting the biofilm formation of Pg, so that the cells can differentiate into osteoblasts. Additionally, JH8194 can increase the formation of mature trabecular bone around the implant and enhance the osseointegration, which is conducive to the long-term stability of the implant. Therefore, JH8194 is an effective drug for antibacterial and osteogenic modification of SIS membrane.

Surprisingly, HST, another member of Hst1, has shown superior ability in healing promotion. Hst1 could promote the migration or adhesion of fibroblasts, epithelial cells and endothelial cells, as well as guide re-epithelialization and vascular regeneration of the wound area. Some studies find that Hst1 binds to G Protein-Coupled Receptors (GPCRs) and activates G protein, which subsequently activates downstream unknown kinases and induces Extracellular Regulated Protein Kinases (Erk 1/2)/Mitogen-Activated Protein (MAP) phosphorylation, eventually promotes cell proliferation and migration. Thus, loading Hst1 may enhance the healing-promoting function of SIS on the basis of JH8194, but the specific mechanism still needs to be explored. Despite these advantages, there still remains a need for a GBR membrane with a good antibacterial effect and an effect of promoting soft tissue healing and/or bone regeneration.

SUMMARY

Technical Problem

In view of the deficiencies existing in the prior arts, the present disclosure provides a chimeric peptide-modified SIS membrane that may simultaneously exert the antibacterial effect and promote soft tissue healing and bone regeneration, which enriches the performance of GBR membrane greatly. The present disclosure has demonstrated that the chimeric peptide-modified SIS membrane (i.e. GBR membrane) is useful for the clinical treatment of infectious bone defects.

Solution to Problem

The present disclosure discloses the following technical solutions:

(1) A chimeric peptide-modified SIS membrane, wherein the sequence of the chimeric peptide comprises at least one sequence in a group consisting of sequences shown as follows:

(i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

In an embodiment, the sequence of the chimeric peptide in (1) comprises a sequence having at least 80% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In a specific embodiment, the sequence of the chimeric peptide in (1) comprises a sequence having 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In another specific embodiment, the sequence of the chimeric peptide in (1) comprises a sequence having 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; and differs from the sequence as set forth in SEQ ID NO: 9, the sequence as set forth in SEQ ID NO: 10, the sequence as set forth in SEQ ID NO: 11, or the sequence as set forth in SEQ ID NO: 12 only in conservative substitution.

(2) The chimeric peptide-modified SIS membrane according to (1), wherein the sequence of the chimeric peptide is composed of at least one sequence in a group consisting of the following sequences:

(i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

In an embodiment, the sequence of the chimeric peptide in (2) has at least 80% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In a specific embodiment, the sequence of the chimeric peptide in (2) has 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In another specific embodiment, the sequence of the chimeric peptide in (2) has 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; and differs from the sequence as set forth in SEQ ID NO: 9, the sequence as set forth in SEQ ID NO: 10, the sequence as set forth in SEQ ID NO: 11, or the sequence as set forth in SEQ ID NO: 12 only in conservative substitution.

(3) The chimeric peptide-modified SIS membrane according to (1) or (2), wherein a method for the modification comprises the following steps:

(a) dissolving the chimeric peptide into a solvent to obtain a solution containing the chimeric peptide;

(b) applying the solution obtained in step (a) to the surface of the SIS membrane; preferably, soaking the SIS membrane in the solution obtained in step (a); and (c) drying the SIS membrane with the solution on the surface thereof.

(4) The chimeric peptide-modified SIS membrane according to any one of (1) to (3), wherein a method for preparing the SIS membrane comprises the following steps:

(i) subjecting a small intestinal submucosa material to primary treatment; and (ii) subjecting the small intestinal submucosa material obtained in step (i) to immunogen removal treatment.

(5) The chimeric peptide-modified SIS membrane according to (4), wherein the method for preparing the SIS membrane further comprises the following steps:

(iii) laminating the small intestinal submucosa material obtained in step (ii); and (iv) subjecting the laminated small intestinal submucosa material to drying treatment.

(6) A method for preparing a chimeric peptide-modified SIS membrane, wherein the method comprises the following steps:

(a) dissolving the chimeric peptide into a solvent to obtain a solution containing the chimeric peptide;

(b) applying the solution obtained in step (a) to the surface of the SIS membrane; preferably, soaking the SIS membrane in the solution obtained in step (a); and (c) drying the SIS membrane with the solution on the surface thereof to obtain the chimeric peptide-modified SIS membrane;

wherein the sequence of the chimeric peptide comprises or is composed of at least one sequence in a group consisting of sequences shown as follows:

(i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

In an embodiment, the sequence of the chimeric peptide in (6) comprises a sequence having at least 80% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; or the sequence of the chimeric peptide in (6) has at least 80% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In a specific embodiment, the sequence of the chimeric peptide in (6) comprises a sequence having 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; or the sequence of the chimeric peptide in (6) has 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12.

In another specific embodiment, the sequence of the chimeric peptide in (6) comprises a sequence having 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; and differs from the sequence as set forth in SEQ ID NO: 9, the sequence as set forth in SEQ ID NO: 10, the sequence as set forth in SEQ ID NO: 11, or the sequence as set forth in SEQ ID NO: 12 only in conservative substitution.

In another specific embodiment, the sequence of the chimeric peptide in (6) has 80%, 81%, 82%, 83%, 84%, 85%, 86%, 87%, 88%, 89%, 90%, 91%, 92%, 93%, 94%, 95%, 96%, 97%, 98% or 99% or more identity to the sequence as set forth in SEQ ID NO: 9, the sequence as set forth in SEQ ID NO: 10, the sequence as set forth in SEQ ID NO: 11, or the sequence as set forth in SEQ ID NO: 12; and differs from the sequence as set forth in SEQ ID NO: 9, the sequence as set forth in SEQ ID NO: 10, the sequence as set forth in SEQ ID NO: 11, or the sequence as set forth in SEQ ID NO: 12 only in conservative substitution.

(7) The preparation method for the chimeric peptide-modified SIS membrane according to (6), wherein a method for preparing the SIS membrane comprises the following steps:

(i) subjecting a small intestinal submucosa material to primary treatment; and (ii) subjecting the small intestinal submucosa material obtained in step (i) to immunogen removal treatment.

(8) The preparation method for the chimeric peptide-modified SIS membrane according to (7), wherein the method for preparing the SIS membrane further comprises the following steps:

(iii) laminating the small intestinal submucosa material obtained in step (ii); and (iv) subjecting the laminated small intestinal submucosa material to drying treatment.

(9) Use of the chimeric peptide-modified SIS membrane according to any one of (1) to (5) or a chimeric peptide-modified SIS membrane obtained by the preparation method for the chimeric peptide-modified SIS membrane according to any one of (6) to (8) in at least one of the following (a) to (d):

(a) serving as or preparing an antibacterial biomaterial;

(b) serving as or preparing an osteogenic biomaterial;

(c) serving as or preparing a healing-promoting biomaterial; and (d) serving as or preparing a biomaterial for treating an infectious bone defect.

(10) A method for treating an infectious bone defect, wherein the method comprises a step of administering, to a subject, the chimeric peptide-modified SIS membrane according to any one of (1) to (5) or a chimeric peptide-modified SIS membrane obtained by the preparation method for the chimeric peptide-modified SIS membrane according to any one of (6) to (8).

Effects of the Invention

In an embodiment, the present disclosure has successfully developed an SIS membrane modified with chimeric peptides, which is used for preparing a chimeric peptide-modified GBR membrane.

In a specific embodiment, the present disclosure uses a set of antibacterial, osteogenic and healing-promoting chimeric peptides which are targeted on the surface of the SIS membrane by collagen binding sequences.

In a specific embodiment, the SIS membrane modified with chimeric peptides in the present disclosure promotes the expression of ITG-α3, ITG-β1, BMP2, RUNX2, ALP and OPN and inhibits the growth of *Streptococcus sanguis* (*S. sanguis*) and *Streptococcus gordonii* (*S. gordonii*) so that the SIS membrane exerts the antibacterial, osteogenic and healing-promoting biological functions.

In a specific embodiment, the SIS membrane modified with chimeric peptides (i.e. the chimeric peptide-modified GBR membrane) used in the present disclosure could be used for the clinical treatment of infectious bone defects.

DETAILED DESCRIPTION

Definitions

Figure 1A:
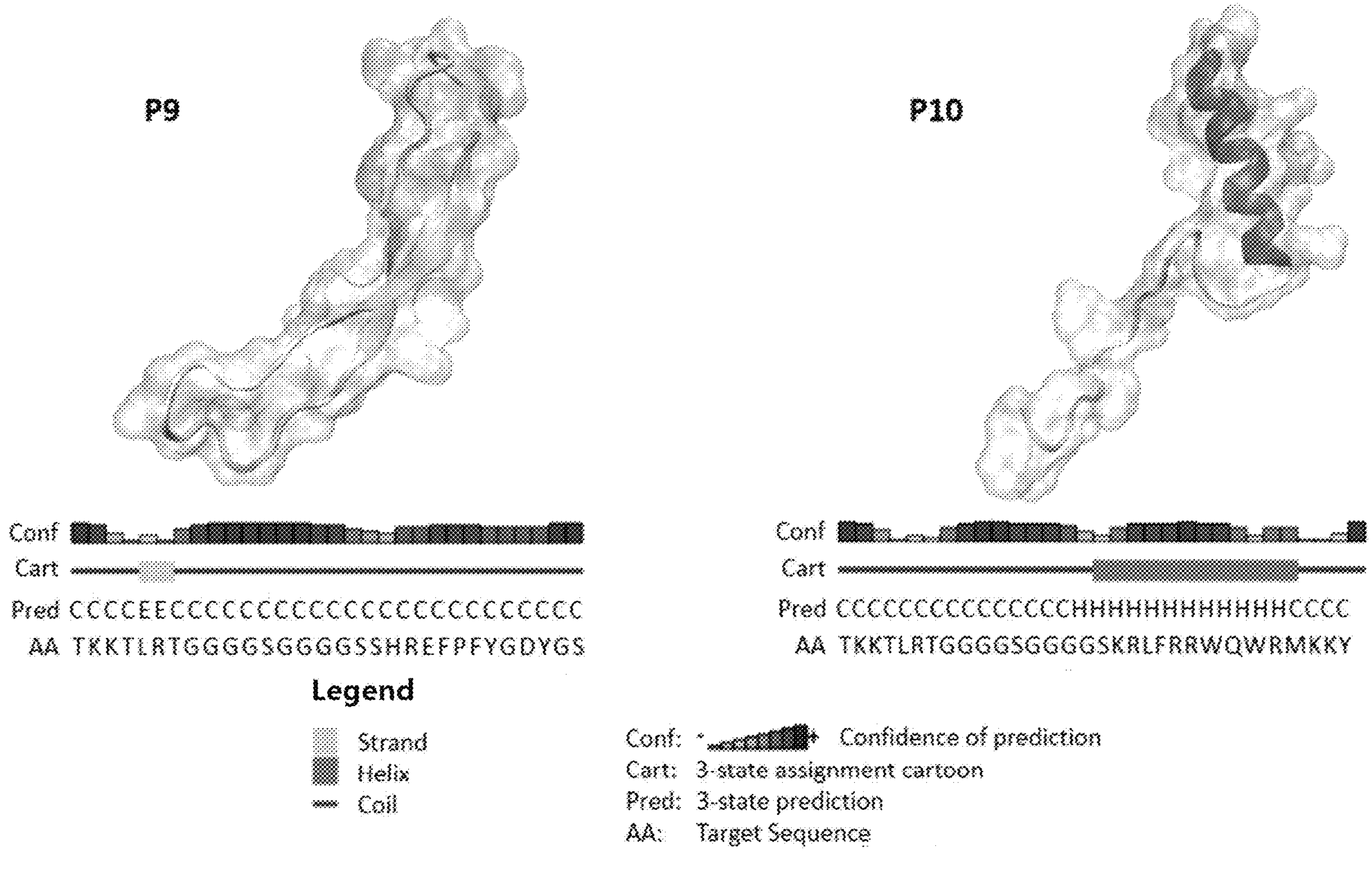
FIG. 1A shows design details and structures of collagen chimeric peptides P9 and P10. The legends are folded strands (Strand), helices (Helix) and random coils (Coil). Conf represents confidence of prediction; Cart represents 3-state assignment cartoon; Pred represents 3-state prediction; and AA represents a target sequence (Target Sequence).

When used in combination with the term "comprising" in the claims and/or specification, the word "a" or "an" may refer to "one" and may also refer to "one or more", "at least one", and "one or more than one".

As used in the claims and specification, the term "including", "having", "comprising" or "containing" is intended to be inclusive or open-ended, and does not exclude additional or unrecited elements or methods and steps.

Throughout the application document, the term "about" means that a value includes a standard deviation or an error caused by the device or method used for determining this value.

It is applicable to the content disclosed herein that the term "or" is defined only as alternatives and "and/or", but the term "or" used in the claims refers to "and/or" unless expressly stated to be only alternatives or mutual exclusion between alternatives.

As used herein, the term "amino acid mutation" or "nucleotide mutation" includes "substitution, repetition, deletion or addition of one or more amino acids or nucleotides". In the present disclosure, the term "mutation" refers to a change in the nucleotide sequence or amino acid sequence. In some embodiments, the "mutation" according to the present disclosure may be selected from "conservative mutation", "semi-conservative mutation", and "non-conservative mutation". In the present disclosure, the term "non-conservative mutation" or "semi-conservative mutation" may be a mutation causing loss or partial loss of the protein function. The term "conservative mutation" refers to a mutation that may normally maintain the functions of a protein. A typical example of the conservative mutation is a conservative substitution.

As used herein, "conservative substitution" usually means an exchange of one kind of amino acid at one or more sites of a protein. Such a substitution may be conservative. Specifically, examples of the substitution taken as the conservative substitution may include a substitution of Ala with Ser or Thr, a substitution of Arg with Gln, His or Lys, a substitution of Asn with Glu, Gln, Lys, His or Asp, a substitution of Asp with Asn, Glu or Gln, a substitution of Cys with Ser or Ala, a substitution of Gln with Asn, Glu, Lys, His, Asp or Arg, a substitution of Glu with Gly, Asn, Gln, Lys or Asp, a substitution of Gly with Pro, a substitution of His with Asn, Lys, Gln, Arg or Tyr, a substitution of Ile with Leu, Met, Val or Phe, a substitution of Leu with Ile, Met, Val or Phe, a substitution of Lys with Asn, Glu, Gln, His or Arg, a substitution of Met with Ile, Leu, Val or Phe, a substitution of Phe with Trp, Tyr, Met, Ile or Leu, a substitution of Ser with Thr or Ala, a substitution of Thr with Ser or Ala, a substitution of Trp with Phe or Tyr, a substitution of Tyr with His, Phe or Trp, and a substitution of Val with Met, Ile or Leu. In addition, conservative mutations further include naturally occurring mutations caused by the difference in individuals from which the genes are derived and the differences in strains and species, etc.

The terms "sequence identity" and "percent identity" used herein refer to the percentage of nucleotides or amino acids that are the same (i.e., identical) between two or more polynucleotides or polypeptides. The sequence identity between two or more polynucleotides or polypeptides may be determined by aligning the nucleotide sequences of polynucleotides or the amino acid sequences of polypeptides and scoring the number of positions at which nucleotide or amino acid residues are identical in the aligned polynucleotides or polypeptides, and comparing the number of these positions with the number of positions at which nucleotide or amino acid residues are different in the aligned polynucleotides or polypeptides. Polynucleotides may differ at one position by, e.g., containing a different nucleotide (i.e., substitution or mutation) or deleting a nucleotide (i.e., insertion or deletion of a nucleotide in one or two polynucleotides). Polypeptides may differ at one position by, e.g., containing a different amino acid (i.e., substitution or mutation) or deleting an amino acid (i.e., insertion or deletion of an amino acid in one or two polypeptides). The sequence identity may be calculated by dividing the number of positions at which nucleotide or amino acid residues are identical by the total number of nucleotide or amino acid residues in the polynucleotides or polypeptides. For example, the percent identity may be calculated by dividing the number of positions at which nucleotide or amino acid residues are identical by the total number of nucleotide or amino acid residues in the polynucleotides or polypeptides, and multiplying the result by 100.

Exemplarily, in the present disclosure, two or more sequences or subsequences, when compared and aligned at maximum correspondence by the sequence alignment algorithm or by the visual inspection measurement, have at least 40%, 50%, 60%, 70%, 80%, 85%, 90%, 91%, 92%, 93%, 94%, 95%, 96%, 97%, 98%, or 99% "sequence identity" or "percent identity" of nucleotide or amino acid residues. The "sequence identity" or "percent identity" may be determined/calculated on the basis of any suitable region of the sequence, for example, a region of at least about 50 residues, a region of at least about 100 residues, a region of at least about 200 residues, a region of at least about 400 residues, or a region of at least about 500 residues in length. In some embodiments, the sequence is substantially identical over the full length of either or both of the compared biopolymers (i.e., nucleic acids or polypeptides).

As used herein, the term "Reverse Complementary Sequence" means a sequence that is opposite to the direction of the sequence of the original polynucleotide and complementary to the sequence of the original polynucleotide. Exemplarily, if the original polynucleotide sequence is ACTGAAC, its reverse complementary sequence is GTTCAGT.

As used herein, the term "polynucleotide" refers to a polymer composed of nucleotides. A polynucleotide may be in the form of an individual fragment, or may be a constituent part of a larger nucleotide sequence structure, which is derived from the nucleotide sequence that has been isolated at least once in number or concentration, and could be recognized, operated, and sequence recovered as well as nucleotide sequence recovered by a standard molecular biological method (e.g., using a cloning vector). When a nucleotide sequence is represented by a DNA sequence (i.e., A, T, G, C), it also includes an RNA sequence (i.e., A, U, G, C), where "U" substitutes for "T". In other words, "polynucleotide" refers to a nucleotide polymer knocked out from an additional nucleotide (an individual fragment or an entire fragment), or may be a constituent part or component of a larger nucleotide structure, such as an expression vector or a polycistronic sequence. Polynucleotides include DNA, RNA, and cDNA sequences. "Recombinant polynucleotide" or "recombinant nucleic acid molecule" is one of "polynucleotides".

As used herein, the term "recombinant nucleic acid molecule" refers to a polynucleotide having sequences that are not joined together in nature. A recombinant polynucleotide may be included in a suitable vector, and the vector may be used for transformation into a suitable host cell. The polynucleotide is then expressed in a recombinant host cell to produce, for example, "recombinant polypeptide", "recombinant protein", or "fusion protein".

As used herein, the terms "linker peptide" and "linker" may be used interchangeably and are capable of linking the same or different polypeptides or amino acids.

The linker peptide includes flexible linker peptides and rigid linker peptides. In the examples of the present disclosure, the linker peptide is a flexible linker peptide. Preferably, the flexible linker peptide is selected from (Gly Gly Gly Gly Ser)$_n$, where n is an integer between 1 and 6; or (Gly Gly Gly Gly Thr)$_n$, where n is an integer between 1 and 6. More preferably, the flexible linker peptide used herein is selected from (Gly Gly Gly Gly Ser)$_2$.

As used herein, the term "high-stringent conditions" means that following the standard DNA blotting procedures, a probe of at least 100 nucleotides in length pre-hybridizes or hybridizes for 12 to 24 hours at 42° C. in 5×SSPE (saline sodium phosphate EDTA), 0.3% SDS, 200 μg/ml of cleaved and denatured salmon sperm DNA, and 50% formamide. Finally, the vector material is washed three times at 65° C. with 2×SSC and 0.2% SDS, each for 15 min.

As used herein, the term "very high-stringent conditions" means that following the standard DNA blotting procedures, a probe of at least 100 nucleotides in length pre-hybridizes or hybridizes for 12 to 24 hours at 42° C. in 5×SSPE (saline sodium phosphate EDTA), 0.3% SDS, 200 μg/ml of cleaved and denatured salmon sperm DNA, and 50% formamide. Finally, the vector material is washed three times at 70° C. with 2×SSC and 0.2% SDS, each for 15 min.

In the present disclosure, unless otherwise emphasized, the terms "chimeric peptide-modified SIS membrane" and "chimeric peptide-modified GBR membrane" have the same meaning and may be used interchangeably.

Unless otherwise defined or clearly indicated by context, all technical and scientific terms used herein have the same meanings as typically understood by one of ordinary skill in the art to which the present disclosure belongs.

Technical Solutions

In the technical solutions of the present disclosure, the meanings denoted by the numbers of the sequence listings of nucleotides and amino acids of the specification are as follows:

SEQ ID NO: 1 shows the amino acid sequence of P1 polypeptide (TKKTLRT+linker-1+Hst8);
SEQ ID NO: 2 shows the amino acid sequence of P2 polypeptide (TKKTLRT+linker-1+JH8195);
SEQ ID NO: 3 shows the amino acid sequence of P3 polypeptide (KELNLVY+linker-1+Hst8);
SEQ ID NO: 4 shows the amino acid sequence of P4 polypeptide (KELNLVY+linker-1+JH8195);
SEQ ID NO: 5 shows the amino acid sequence of P5 polypeptide (TKKTLRT+linker-1+Hst7);
SEQ ID NO: 6 shows the amino acid sequence of P6 polypeptide (TKKTLRT+linker-1+JH8944);
SEQ ID NO: 7 shows the amino acid sequence of P7 polypeptide (KELNLVY+linker-1+Hst7);
SEQ ID NO: 8 shows the amino acid sequence of P8 polypeptide (KELNLVY+linker-1+JH8944);
SEQ ID NO: 9 shows the amino acid sequence of P9 polypeptide (TKKTLRT+linker-1+Hst1);
SEQ ID NO: 10 shows the amino acid sequence of P10 polypeptide (TKKTLRT+linker-1+JH8194);
SEQ ID NO: 11 shows the amino acid sequence of P11 polypeptide (KELNLVY+linker-1+Hst1);
SEQ ID NO: 12 shows the amino acid sequence of P12 polypeptide (KELNLVY+linker-1+JH8194);
SEQ ID NO: 13 shows the amino acid sequence of P13 polypeptide (TKKTLRT+linker-2+Hst1);
SEQ ID NO: 14 shows the amino acid sequence of P14 polypeptide (TKKTLRT+linker-2+JH8194);
SEQ ID NO: 15 shows the amino acid sequence of P15 polypeptide (KELNLVY+linker-2+Hst1);
SEQ ID NO: 16 shows the amino acid sequence of P16 polypeptide (KELNLVY+linker-2+JH8194).

Unless otherwise emphasized, the steps of the following general experimental methods (A) to (E) employed in the examples of the present disclosure are as follows:

(A) Methods for Preparing SIS and Chimeric Peptide-Modified SIS Membranes:

The preparation method for the SIS membrane is as follows:

(i) Primary Treatment of Small Intestinal Submucosa Materials

Small Intestinal Submucosa (SIS) materials are taken and subjected to primary treatment.

In a specific embodiment, the abovementioned primary treatment of the present disclosure comprises the steps of dividing, cleaning and/or viral inactivating the SIS materials.

As for the viral inactivation, the low-concentration peracetic acid-ethanol solution method may be used to inactivate viruses. This step may be carried out in an ultrasonic cleaner, in which the content of the peracetic acid may be 0.05 to 0.2% by volume, the ultrasonic oscillation frequency may be 30 to 600 rpm, the ultrasonic frequency may be 20 to 80 KHZ, and the temperature range is 4 to 40° C. Thereafter, the materials are cleaned in water or a phosphate buffer.

(ii) Immunogen Removal Treatment

The immunogen may be removed from the small intestinal submucosa material treated in step (i) by physical, chemical and/or biological methods. Methods including a freeze-thaw method, a hypotonic and hypertonic method, an acid-base dissolution method, a detergent method, and an enzymic method may be taken for removal. The immunogen may also be removed by a combination of multiple methods. An ultrasonic-assisted method is preferred, for example, it may be carried out in an ultrasonic cleaner. Firstly the small intestinal submucosa material treated in step (i) is put in a cleaning tank, to which a decellularized solution is injected for treatment, for example, an alkaline solution, a saline solution or an enzyme-containing solution. The treated material is cleaned.

The small intestinal submucosa material treated in step (ii) may be used as a membrane material of the chimeric peptide-modified SIS membrane.

In another specific embodiment, it is also possible to improve the thickness and strength of the membrane material by laminating the small intestinal submucosa material treated in (ii) described previously.

In another specific embodiment, for the ease of transport and treatment, the laminated material described above may be further subjected to drying treatment. The drying treatment includes freeze-drying and/or normal-temperature drying treatment.

The preparation method for the chimeric peptide-modified SIS membrane is as follows:

The SIS membranes are cut into circles matched with different culture plates size and soaked in chimeric peptide solutions at a low concentration (50 μM), a medium concentration (100 μM), and a high concentration (200 μM) for 10 min. Subsequently, the membranes are taken out and frozen overnight, and then lyophilized to generate a chimeric peptide-modified SIS membrane (pSIS). In the subsequent exemplary experiments, L-pSIS is used to represent the SIS membrane soaked in a low-concentration chimeric peptide solution, M-pSIS is used to represent the SIS membrane soaked in a medium-concentration chimeric peptide solution, and H-pSIS is used to represent the SIS membrane soaked in a high-concentration chimeric peptide solution. In this treatment process, 50 μM, 100 μM, and 200 μM chimeric peptide solutions are used as schematic controls, instead of limiting the concentration of the chimeric peptide solution.

In another specific embodiment, other methods may also be adopted to modify chimeric peptides onto the surface of the SIS membrane, for example, a chimeric peptide-containing solution is applied to the surface of the SIS membrane by such a method as coating, spraying or transferring, and then subjected to drying treatment.

(B) Method for qRT-PCR Analysis in Cell Culture:

Total cellular RNA is extracted by using Trizol (Gibco, USA). cDNA is synthesized using GoScript™ Reverse Transcription Mix (Promega, USA). The qRT-PCR analysis is performed on the Roche LC480II system (Roche, Switzerland) using a GoTaq qPCR Master Mix (Promega, USA). The data is calculated using GAPDH as the internal control by the $^{\Delta\Delta}$Ct method. The sequences of primers are listed in Table 5.

TABLE 5

Primer Sequences of Real-time PCR

| Genes | Primer Sequences (5'-3') |
|---|---|
| Bmp2 | F: TGCGGTCTCCTAAAGGTCG (SEQ ID NO: 17) R: ACTCAAACTCGCTGAGGACG (SEQ ID NO: 18) |
| Runx2 | F: CCGAACTGGTCCGCACCGAC (SEQ ID NO: 19) R: CTTGAAGGCCACGGGCAGGG (SEQ ID NO: 20) |
| Alp | F: AGGCAGGATTGACCACGG (SEQ ID NO: 21) R: TGTAGTTCTGCTCATGGA (SEQ ID NO: 22) |
| Opn | F: AATGAAGGGCCCTGAGC (SEQ ID NO: 23) R: GCCAGTTCTGCAAGGAAGC (SEQ ID NO: 24) |
| Gapdh | F: GACGGCCGCATCTTCTTGTGC (SEQ ID NO: 25) R: TGCAAATGGCAGCCCTGGTGA (SEQ ID NO: 26) |

TABLE 5-continued

Primer Sequences of Real-time PCR

| Genes | Primer Sequences (5'-3') |
|---|---|
| ITG-β1 | F: CCTACTTCTGCACGATGTGATG (SEQ ID NO: 27) R: CCTTTGCTACGGTTGGTTACATT (SEQ ID NO: 28) |
| ITG-α3 | F: CTACCACAACGAGATGTGCAA (SEQ ID NO: 29) R: CCGAAGTACACAGTGTTCTGG (SEQ ID NO: 30) |
| GAPDH | F: GGAGCGAGATCCCTCCAAAAT (SEQ ID NO: 31) R: GGCTGTTGTCATACTTCTCATGG (SEQ ID NO: 32) |

(C) Method for Western Blot Analysis in Cell Culture:

After culturing, proteins are separated by electrophoresis and transferred to polyvinylidene fluoride (PVDF) membranes (Sigma-Aldrich, USA). After being blocked with 5% bovine serum albumin (BSA, Sigma-Aldrich, USA) at room temperature for 1 h, PVDF membranes are probed with 1:1000 primary antibodies (Abcam, UK) at 4° C. overnight. Then, they are incubated with corresponding secondary antibodies at 1:5000 dilution for 60 min at room temperature. A Pierce™ ECL Western Blotting Substrate (Thermo Fisher Scientific, USA) is used to detect antibody-bound proteins. Image J software is used for quantitative analysis.

(D) Method for Immunofluorescence Staining in Cell Culture:

$1\times10^4$ BMSCs (Bone Mesenchymal Stem Cells) or OECs are seeded onto 24-well plates cultured with 1 mL leaching solution of SIS, M-pSIS or H-pSIS membranes and then BMSCs are cultured with osteoinductive medium. After the corresponding culture period, BMSCs or OECs are fixed in 4% formaldehyde for 30 min, permeabilized with 0.5% Triton X-100 for 5 min and blocked in 5 mg/mL BSA solution for 1 h. Then, cells are incubated with primary antibodies (Abcam, UK) at 1:200 dilution at 37° C. for 2 h. After that, they are incubated with Cy3-conjugated anti-rabbit/mouse secondary antibody at 1:200 dilution (Abcam, UK) for 1 h, and then stained with 1 mg/mL DAPI (Solarbio, China) for 10 min. CLSM is used to visualize.

(E) Method for Statistical Analysis:

All experimental data are expressed as means±standard deviations (SD) which repeat at least three times. Statistical analysis is assessed using single factor analysis of variance (ANOVA) of variance with Turkey's test. A p-value less than 0.05 is considered to have significant statistical difference (*$p<0.05$).

EXAMPLES

Other purposes, features, and advantages of the present disclosure will become apparent from the following detailed description. It should be appreciated, however, that the detailed description and specific examples (while representing the specific embodiments of the present disclosure) are only provided for illustrative purposes because various variations and modifications made within the spirit and scope of the present disclosure will become apparent to a person skilled in the art after reading the detailed description.

The experimental techniques and experimental methods used in the present examples, unless otherwise specified, are all conventional techniques and methods, for example, experimental methods for which no specific conditions are indicated in the following examples are generally performed according to conventional conditions such as those described by Sambrook et al., *Molecular Cloning: A Laboratory Manual* (New York: Cold Spring Harbor Laboratory Press, 1989), or those recommended by manufacturers. The materials, reagents, etc. used in the examples, unless otherwise specified, are all commercially available.

Example 1: Design and Synthesis of Chimeric Peptide

In order to verify the difference in activities of chimeric peptides, the present disclosure designed combinations comprising multiple sets of chimeric peptides with different functions.

The chimeric polypeptides involved in the present disclosure were synthesized by Jill biochemical Shanghai Co., Ltd., China.

The groupings and specific sequences of the chimeric polypeptides involved in the present disclosure were as follows:

Control-1: collagen binding peptides (type I: TKKTLRT; type III: KELNLVY); flexible Linker: GGGGSGGGGS; functional peptides: Hst8/JH8195. The sequences of four chimeric peptides in Control-1 were listed in Table 1.

TABLE 1

Sequences of Chimeric Peptides in Control-1

| Control-1 | Combination Modes | Polypeptide Sequences |
|---|---|---|
| P1 | TKKTLRT + linker-1 + Hst8 | TKKTLRTGGGG SGGGGSKFHEK HHSHRGY |
| P2 | TKKTLRT +linker-1 + JH8195 | TKKTLRTGGGG SGGGGSKRLFR RLLFSMKKY |
| P3 | KELNLVY + linker-1 + Hst8 | KELNLVYGGGG SGGGGSKFHEK HHSHRGY |
| P4 | KELNLVY + linker-1 + JH8195 | KELNLVYGGGG SGGGGSKRLFR RLLFSMKKY |

Control-2: collagen binding peptides (type I: TKKTLRT; type III: KELNLVY); flexible Linker: GGGGSGGGGS; functional peptides: Hst7/JH8944.
The sequences of four chimeric peptides in Control-2 were listed in Table 2.

TABLE 2

Sequences of Chimeric Peptides in Control-2

| Control-2 | Combination Modes | Polypeptide Sequences |
|---|---|---|
| P5 | TKKTLRT + linker-1 + Hst7 | TKKTLRTGGGG SGGGGSRKFHE KHHSHRGY |
| P6 | TKKTLRT + linker-1 + JH8944 | TKKTLRTGGGG SGGGGSFKCKK VVISLRRY |
| P7 | KELNLVY + linker-1 + Hst7 | KELNLVYGGGG SGGGGSRKFHE KHHSHRGY |

TABLE 2-continued

Sequences of Chimeric Peptides in Control-2

| Control-2 | Combination Modes | Polypeptide Sequences |
|---|---|---|
| P8 | KELNLVY + linker-1 + JH8944 | KELNLVYGGGG SGGGGSFKCKK VVISLRRY |

pSIS-1: collagen binding peptides (type I: TKKTLRT; type III: KELNLVY); flexible Linker: GGGGSGGGGS; functional peptides: Hst1/JH8194; the sequences of four chimeric peptides in pSIS-1 were listed in Table 3.
Hst1 had a degree of healing activity, and JH8194 had a degree of osteogenic activity and antibacterial activity.

TABLE 3

Sequences of Chimeric Peptides in pSIS-1

| pSIS-1 | Combination Modes | Polypeptide Sequences |
|---|---|---|
| P9 | TKKTLRT + linker-1 + Hst1 | TKKTLRTGGG GSGGGGSSHR EFPFYGDYGS |
| P10 | TKKTLRT + linker-1 + JH8194 | TKKTLRTGGG GSGGGGSKRL FRRWQWRMKK Y |
| P11 | KELNLVY + linker-1 + Hst1 | KELNLVYGGG GSGGGGSSHR EFPFYGDYGS |
| P12 | KELNLVY + linker-1 + JH8194 | KELNLVYGGG GSGGGGSKRL FRRWQWRMKKY |

pSIS-2: collagen binding peptides (type I: TKKTLRT; type III: KELNLVY); rigid Linker: EAAAKEAAAK; functional peptides: Hst1/JH8194; the sequences of four chimeric peptides in pSIS-2 were listed in Table 4.

TABLE 4

Sequences of Chimeric Peptides in pSIS-2

| pSIS-2 | Combination Modes | Polypeptide Sequences |
|---|---|---|
| P13 | TKKTLRT + linker-2 + Hst1 | TKKTLRTEAAAK EAAAKSHREFPF YGDYGS |
| P14 | TKKTLRT + linker-2 + JH8194 | TKKTLRTEAAAK EAAAKKRLFRRW QWRMKKY |
| P15 | KELNLVY + linker-2 + Hst1 | KELNLVYEAAAK EAAAKSHREFPF YGDYGS |
| P16 | KELNLVY + linker-2 + JH8194 | KELNLVYEAAAK EAAAKKRLFRRW QWRMKKY |

Example 2: Structure Prediction of pSIS Chimeric Peptides

It should be noted that the pSIS in Example 2 corresponded to the pSIS-1 in Example 1. Chimeric peptides were synthesized by the Fmoc solid-phase peptide synthesis (Jill biochemical Shanghai Co., Ltd., China) according to the sequences listed in Table 3 until the purity was 95%. P9 and P10 were labeled with FITC and P11 and P12 were labeled with RB for CLSM. The secondary structures were analyzed by the software PSIPRED. The tertiary structures were predicted by the protein analysis software Robetta and visualized by VMD.

The structures of P9, P10, P11, and P12 were predicted by PSIPRED and Robetta. The chimeric peptides were composed of three parts: P9 and P10: TKKTLRT (binding to type I collagen of the SIS membrane), Hst1/JH8194 (playing antibacterial, osteogenic and healing-promoting functions) and GGGGSGGGGS (linking the first two parts), P11 and P12: KELNLVY (binding to type III collagen of the SIS membrane), Hst1/JH8194, and GGGGSGGGGS.

Figure 1B:
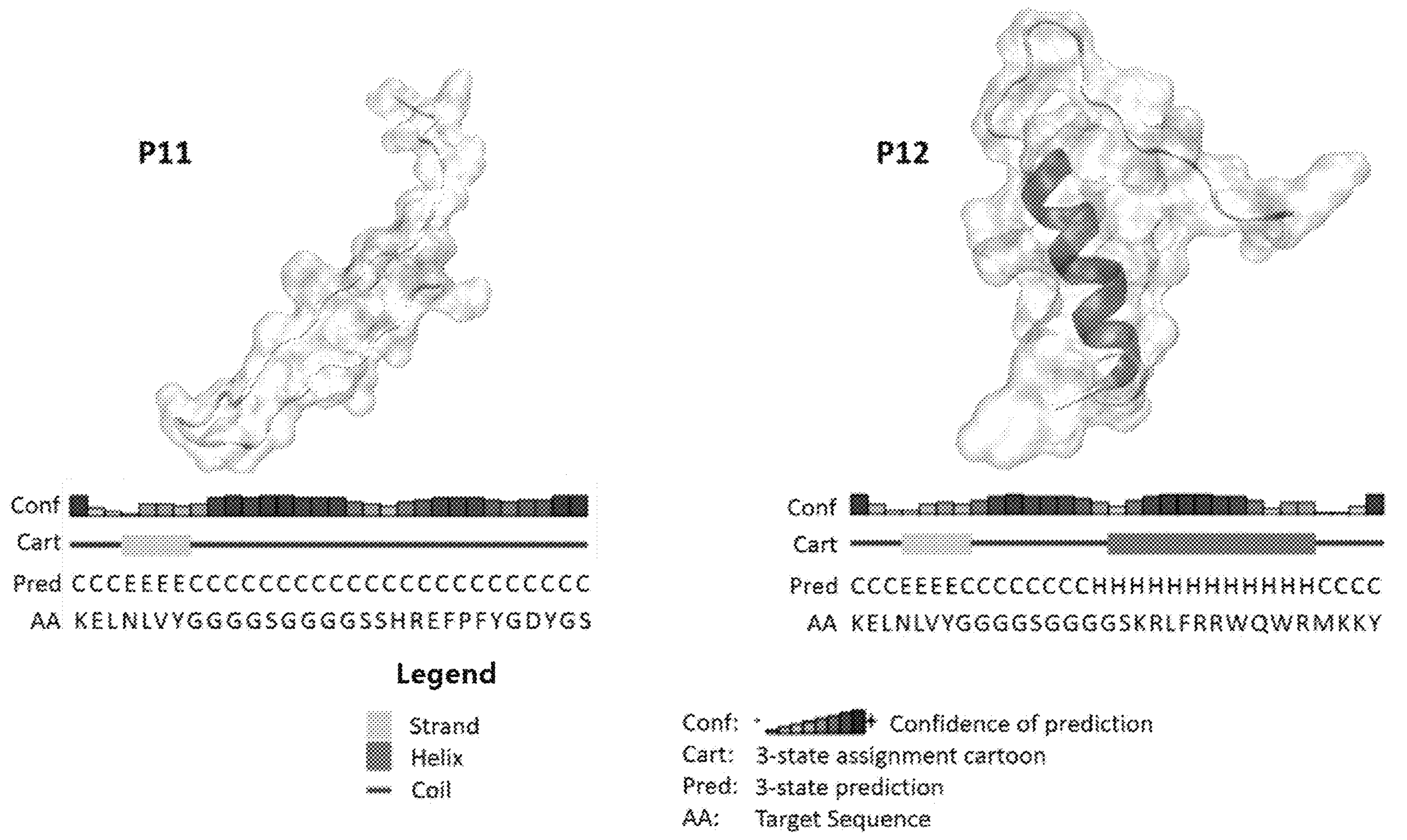
FIG. 1B shows design details and structures of collagen chimeric peptides P11 and P12. The legends are folded strands (Strand), helices (Helix) and random coils (Coil). Conf represents confidence of prediction; Cart represents 3-state assignment cartoon; Pred represents 3-state prediction; and AA represents a target sequence (Target Sequence).

FIG. 1A shows design details and structures of collagen chimeric peptides P9 and P10. FIG. 1B shows design details and structures of collagen chimeric peptides P11 and P12. The four chimeric peptides were composed of collagen binding peptides (TKKTLRT or KELNLVY), functional peptides (Hst1 or JH8194) and a flexible Linker (GGGGSGGGGS). "GGGGS" was the most commonly used flexible linker consisting of glycine (Gly) and serine (Ser) residues, which could ensure the flexibility and mobility of connecting functional domains. In the present disclosure, the copy number of "GGGGS" is preferably 2 to achieve appropriate separation of the functional domains and avoid mutual interference.

The results of FIG. 1A and FIG. 1B showed that all of P9 to P12 has one or several basic structures, such as α-helix, β-sheet and radon coils, and their spatial structures were different.

Example 3: Fabrication, Morphological Observation, and Biocompatibility of Chimeric Peptide-Modified SIS Membrane (pSIS)

It should be noted that the pSIS in Example 3 corresponded to the pSIS-1 in Example 1.

The SIS membranes were cut into circles matched with culture plates with different sizes and soaked in chimeric peptide solutions at a low concentration (50 μM), a medium concentration (100 μM), and a high concentration (200 μM) for 10 min. Subsequently, the membranes were taken out and frozen overnight, and then lyophilized to generate a chimeric peptide-modified SIS membrane (pSIS). Samples were labeled as L-pSIS group, M-pSIS group, and H-pSIS group. After sputter-coated with gold, the surface morphology of the SIS and pSIS membranes was observed by SEM (Gemini 300, Zeiss, Germany).

In addition, $1\times10^4$ BMSCs or OECs in 1000 μL of Dulbecco's modified Eagle medium (DMEM, Gibco, USA) with 10% fatal bovine serum (FBS, Gibco, USA) were seeded onto the 24-well plates and cultured at 37° C. with 5% $CO_2$. After 1, 2, 4, and 6 days, 100 μL of CCK-8 solutions (Solarbio, China) were added to each sample. After incubated at 37° C. with 5% $CO_2$ for 4 h, the relative cell viability was determined by measuring the light absorbance (OD) at 450 nm.

Figure 2A:
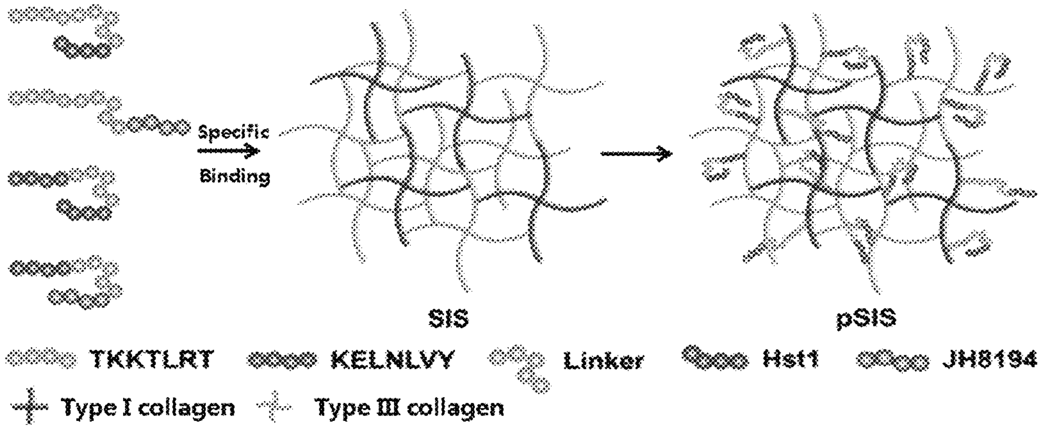
FIG. 2A shows a schematic diagram of a pSIS membrane.
Figure 2B:
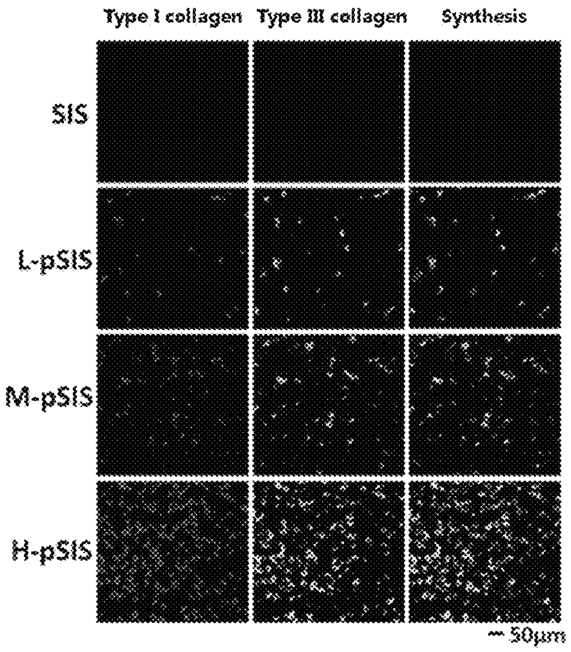
FIG. 2B shows binding of chimeric peptides observed by CLSM.
Figure 2C:
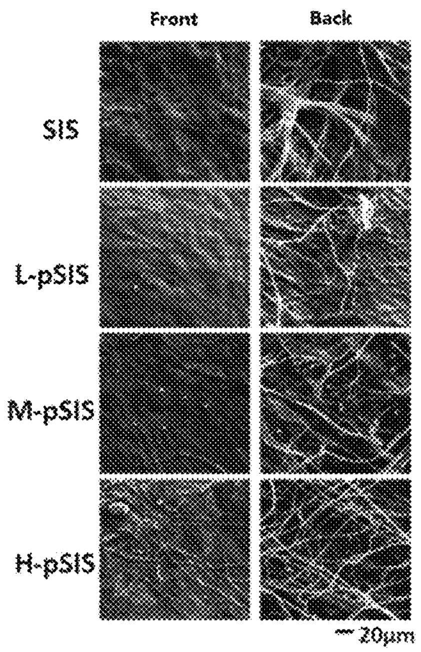
FIG. 2C shows the surface morphology of freeze-drying SIS and pSIS observed by SEM.
Figure 2D:
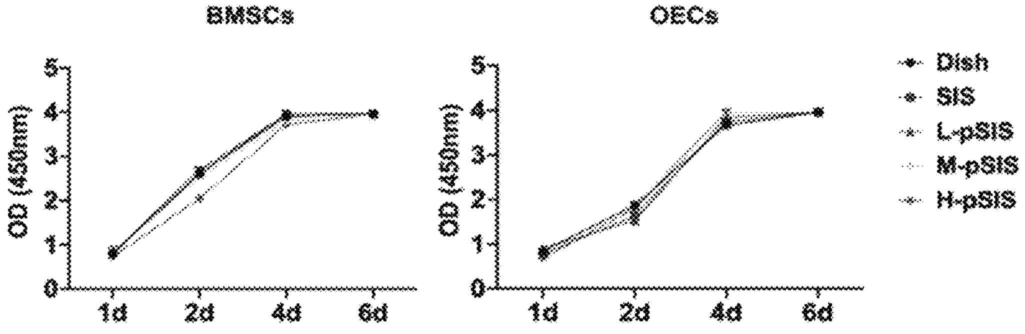
FIG. 2D shows proliferation abilities of BMSCs and OECs by CCK-8.

FIG. 2A shows a schematic diagram of a pSIS membrane. FIG. 2B shows binding of chimeric peptides observed by CLSM. P9 and P10 were labeled with rhodamine B (RB), and P11 and P12 were labeled with fluorescein isothiocyanate (FITC). FIG. 2C shows the surface morphology of freeze-drying SIS and pSIS observed by SEM. Meanings of different representations were as follows: SIS: soaked in PBS; L-pSIS: soaked in 50 μM chimeric peptide solution; M-pSIS: soaked in 100 μM chimeric peptide solution; H-pSIS: soaked in 200 μM chimeric peptide solution. FIG. 2D shows proliferation abilities of BMSCs and OECs by CCK-8.

Subsequently, the SIS membranes were soaked in 50 μM (L-pSIS), 100 μM (M-pSIS) and 200 μM (H-pSIS) chimeric peptide solutions to observe the binding of chimeric peptides on the surface of the SIS membrane. Confocal laser scanning microscopy (CLSM) and scanning electron microscopy (SEM) were used for detection. With the concentration increasing, the fluorescent label on the SIS membrane increased (FIG. 2B), indicating that more chimeric peptides were bound. In particular, after soaking with 200 μM chimeric peptide solution, more than 85% fluorescent area of the SIS membrane (H-pSIS) realized the effective binding. Then, the surface morphology of pSIS after freeze-drying was observed by SEM (FIG. 2C). Compared with SIS, pSIS still maintained a similar structure and had small particle-like substances formed by specific combination of a large number of chimeric peptides with SIS membrane. Lyophilization process did not affect the structure of the SIS membrane and the stable binding of chimeric peptides. The higher the concentration of chimeric peptide solution, the more particles on the surface of pSIS. However, because of the minuscule molecular weight of chimeric peptides, SEM could only observe a large number of aggregated particles, which might not match the binding rate observed under CLSM.

Biocompatibility, the interaction between material and host, is a fundamental characteristic of materials to ensure the safety of patients during application. The effects of pSIS on cell proliferation over time were explored by CCK-8. It showed that BMSCs and OECs proliferated logarithmically on the surface of pSIS (FIG. 2D). On the second day, the proliferation ability of BMSCs on H-pSIS membrane was lower than other groups significantly, but with the time prolongation, the proliferation ability increased and there was no statistical difference with other groups. It was found that pSIS had no significant effect on the proliferation of BMSCs or OECs, providing a guarantee for their further application. Therefore, taken the results of CLSM, SEM and CCK-8 into consideration, M-pSIS and H-pSIS with higher binding rate of chimeric peptides were selected for further exploration in the subsequent experiments.

Example 4: Antibacterial Activity of pSIS In Vitro

It should be noted that the pSIS in Example 4 corresponded to the pSIS-1 in Example 1. *S. sanguis* (ATCC 10556) and *S. gordonii* (ATCC 51656) were cultured in brain heart infusion (BHI) agar plates for 18 h at 37° C. Then, the bacteria were resuspended at $1\times10^7$ CFU/ml (CFU, colony forming units) as a primary inoculum. In a 100 mm bacterial culture dish, 20 ml of BHI solution mixed with 100 μl of bacterial solution was inoculated. After coagulation, the SIS, M-pSIS and H-pSIS membranes were placed in the center, and the blank well was used as the control. After 24 h, the inhibitory rings were observed and photographed.

In addition, after the primary inoculum was inoculated and incubated on the SIS, M-PSIS and H-pSIS membranes for 24 h, the membranes were washed with PBS three times and then stained with the Live/dead staining kit (Life Technologies Corporation, CA) on new plates. The dead bacteria, live bacteria, and Alexa Fluor 405 labeled-peptides could be observed by CLSM.

Figure 3A:
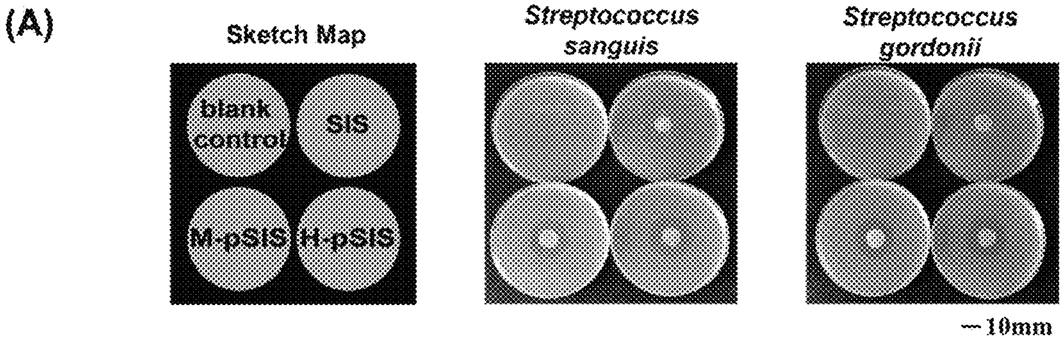
FIG. 3A shows inhibitory rings of *S. sanguis* and *S. gordonii.*
Figure 3B:
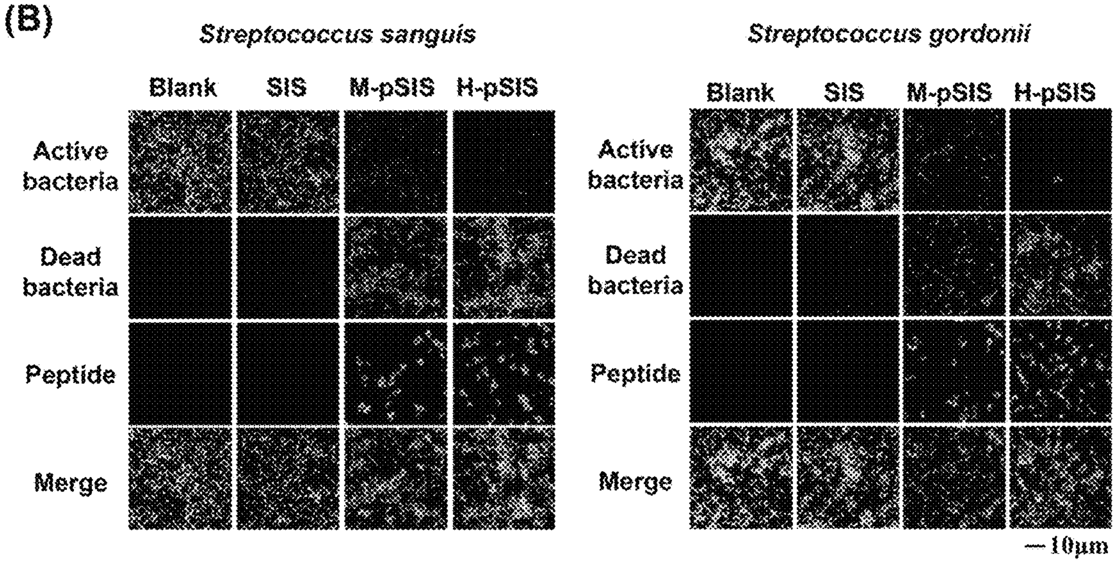
FIG. 3B shows CLSM images of staining after culturing mixed bacteria in a blank well, SIS, M-pSIS or H-pSIS for 24 h.

FIG. 3A shows inhibitory rings of *S. sanguis* and *S. gordonii* (upper left: blank control; upper right: SIS; lower left: M-pSIS; lower right: H-pSIS). FIG. 3B shows CLSM images of staining after culturing mixed bacteria in a blank well, SIS, M-pSIS or H-pSIS for 24 h.

To investigate the antibacterial activity of pSIS against *S. sanguis* and *S. gordonii*, inhibitory ring and CLSM were detected (FIG. 3A and FIG. 3B). Although SIS could produce tiny inhibitory rings, the results were not statistically significant, while M-pSIS and H-pSIS could produce obvious inhibitory rings for two kinds of bacteria (FIG. 3A). Additionally, the CLSM images showed the live/dead colonies of bacteria (FIG. 3B). Compared with the blank well, the SIS group had a small number of dead bacteria. Conversely, with the increase of peptide concentration, dead bacteria of M-pSIS and H-pSIS increased sequentially, indicating that chimeric peptides enhanced the antibacterial activity of the SIS membrane and H-pSIS was the strongest.

Plaque biofilms were multispecies microbial communities which could enhance the resistance of bacteria to host defense system and antimicrobial agents, finally leading to inflammation. *S. gordonii* and *S. sanguis* were early colonizing bacteria of dental plaque biofilm. Timely and early control of the above flora colonization would be conducive to the prevention of oral infection and inflammation after GBR operation. JH8194 was a derivative peptide of oral antimicrobial peptide Hst5. AMP and derivatives thereof could exchange divalent cations (e.g. $Mg^{2+}$ and $Ca^{2+}$) on the bacterial membrane via an "ion-exchange mechanism" to disrupt the stability of cytoplasmic membrane, leading to cell death. Moreover, the positively charged AMPs could absorb on the negatively charged cytoplasmic membrane through electrostatic interaction, and insert into phospholipid bimolecular layer to form pores or even larger defect on the membrane, eventually resulting in cytoplasmic leakage and bacterial death.

Example 5: Effect of pSIS on Osteogenic-Related Factors Expression of BMSCs

It should be noted that the pSIS in Example 5 corresponded to the pSIS-1 in Example 1.

Assay of cell migration activity of pSIS in vitro:

SIS, M-pSIS or H-pSIS membranes and 500 μL of medium (2% FBS) were put into the lower compartment of the transwell plate, and the blank well containing only medium served as the control. Then, $1\times10^4$ OECs in 500 μL of medium (2% FBS) were seeded onto transwell inserts (Thermo Fisher Scientific, USA). After 24 h, media within the transwell inserts were removed carefully. Cells were fixed with 4% paraformaldehyde for 30 min, permeabilised with 0.01% Triton X-100 (Sigma-Aldrich, USA) for 5 min and stained with 1% crystal violet (Sigma-Aldrich, USA). The cells without migration were removed by gently wiping with a cotton swab. Then, migrated cells were viewed and imaged with an inverted fluorescence microscope (Olympus IX71, Japan).

$1\times10^5$ OECs were seeded onto 6-well plates with sterilized SIS, M-pSIS and H-pSIS membranes and cultured for 24 h. Then, the cells were scraped down by a cell scraper and collected by 1000 rpm centrifugation for 3 min. Each sample required $1\times10^6$ OECs. Subsequently, differentially expressed genes were commercially detected by RNA-seq (Beijing Nuohe Zhiyuan biological Mdt InfoTech Ltd., China). Quantitative real-time polymerase chain reaction (qRT-PCR) analysis, Western Blot analysis and immunofluorescence staining were used to detect differentially expressed factors after OECs were cultured for 24 h.

Assay of Osteogenic Activity of pSIS In Vitro:

Animal experiments in the present disclosure were approved by the Animal Ethical Committee of the Academic Medical Center at the Tianjin Medical University. Briefly, the experiment was divided into blank control, SIS, Bio-Gide, and H-pSIS groups. The Sprague-Dawley (SD) rats (250 to 280 g, male, 6-8 weeks) were anesthetized by inhaling isoflurane. Then, the Parietal Calvarium was exposed by cutting skin. Subsequently, a full-thickness defect with a diameter of 8 mm was made in the center of the skull with a trephine. No treatment was made in the blank control group, and the corresponding membranes were placed on the defects in the other three groups. Finally, the wound was stitched up.

At the end of 12 weeks, the rats were euthanasia. The bone defects were taken out and fixed in 4% paraformaldehyde for 24 h. Then, the samples were scanned with Micro-CT (SkyScan 1276, Germany) for standardized reconstruction and evaluating new bone formation. Next, the samples were decalcified with a rapid decalcifying fluid (Rapid Cal Immuno, ZS-Bio, China) for 7 d. After being dehydrated and paraffin-embedded, the samples were sliced at 5 μm in thickness. H&E and Masson's trichrome staining (Solarbio, China) were used for histological analysis. The primary antibody anti-OCN, anti-COL1 and fluorescence-conjugated secondary antibody IgG at 1:200 dilution (Abcam, UK) were used for immunohistochemistry. The sections were observed using a Quantitative Analysis System for Whole Landscape Imaging of Tissue Slices (Vectra Polaris, PerkinElmer, USA).

The osteoinductive medium containing 10 mM β-glycerophosphate (Sigma, USA), 100 nM dexamethasone (Sigma, USA) and 50 μM ascorbate (Sigma, USA) was prepared. $1\times10^5$ BMSCs were inoculated on sterilized SIS, M-pSIS and H-pSIS membranes in 6-well plates for culturing 3 days with culture medium, and then the osteoinductive medium was used instead. After 7, 14 and 21 days, the expression of BMP2, RUNX2, ALP and OPN was detected.

Figure 4A:
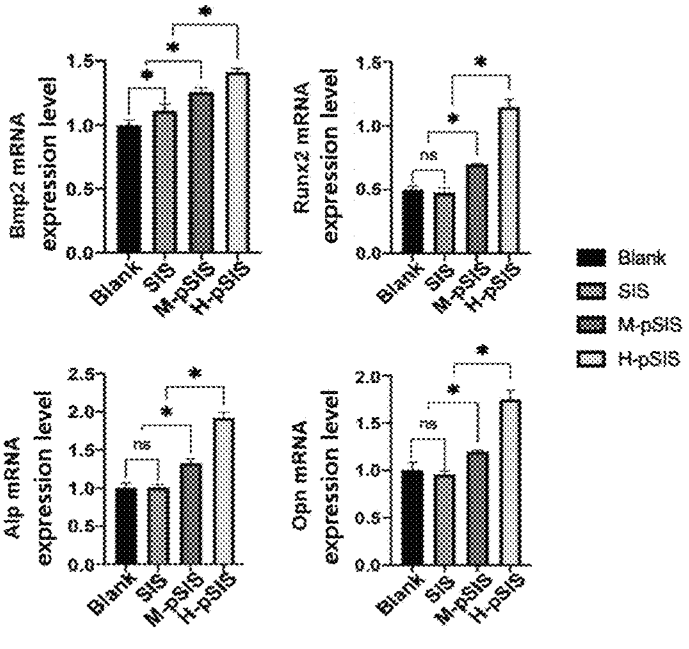
FIG. 4A shows the results of qPCR analysis of osteogenic-related genes (* represents $p<0.05$).
Figure 4B:
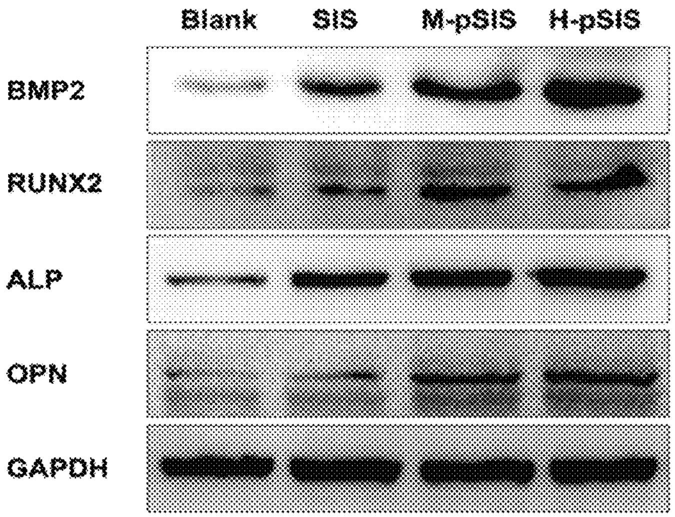
FIG. 4B shows the results of Western Blot analysis of osteogenic-related proteins.
Figure 4C:
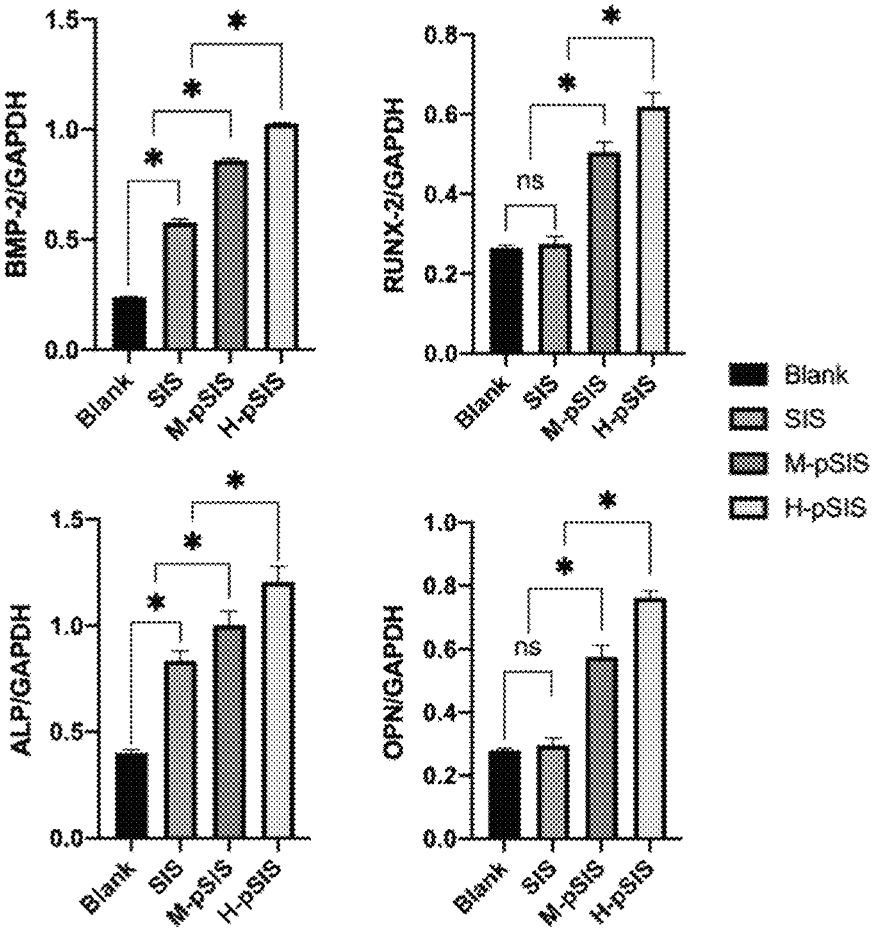
FIG. 4C shows the results of quantitative analysis of Western Blot analysis (* represents $p<0.05$).
Figure 4D:
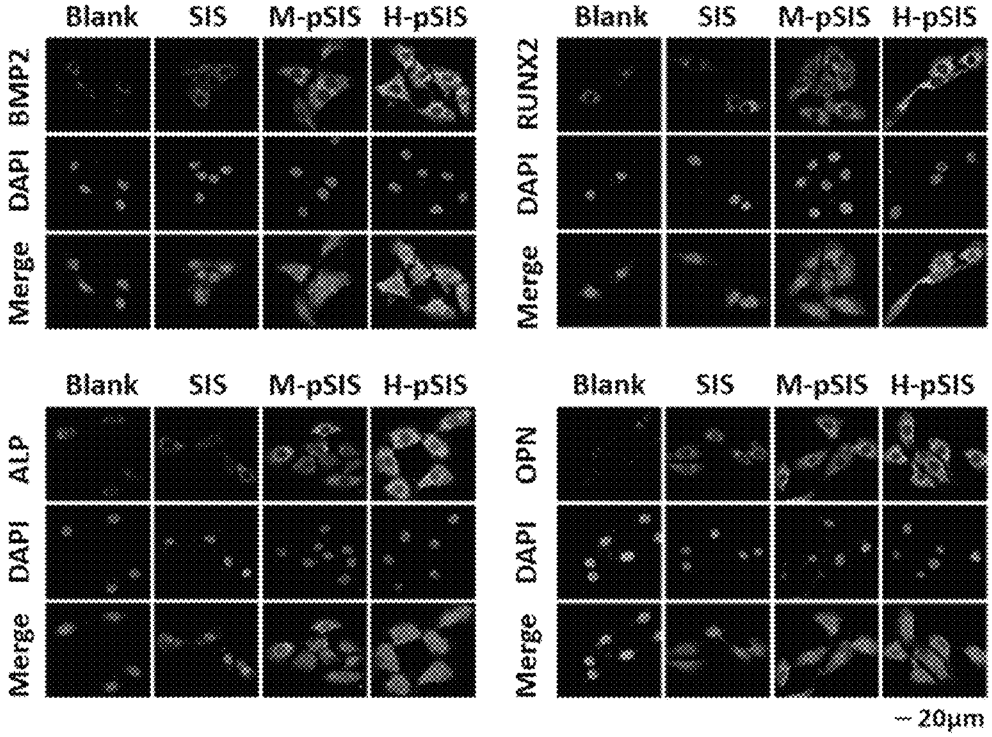
FIG. 4D shows the results of immunofluorescence analysis of osteogenic-related proteins localizations in BMSCs (BMP2, RUNX2, ALP, OPN, and nucleus).

FIG. 4A shows the results of qPCR analysis of osteogenic-related genes (* represents $p<0.05$). FIG. 4B shows the results of Western Blot analysis of osteogenic-related proteins. FIG. 4C shows the results of quantitative analysis of Western Blot analysis (* represents $p<0.05$). FIG. 4D shows the results of immunofluorescence analysis of osteogenic-related proteins localizations in BMSCs (BMP2, RUNX2, ALP, OPN, and nucleus).

Osteogenesis was the key of GBR technology. The effect of pSIS on the expression of osteogenic-related factors of BMSCs was also assessed (FIG. 4A to FIG. 4D). Bone morphogenetic protein-2 (BMP2), Runt-related transcription factor 2 (RUNX2), alkaline phosphatase (ALP) and osteopontin (OPN) were classical osteogenic factors. As shown in FIG. 4A, the mRNA levels of the above osteogenic factors of pSIS groups were significantly higher than blank control and SIS. Similarly, Western Blot analysis also confirmed this trend (FIG. 4B and FIG. 4C), indicating that the chimeric peptide-modified SIS membrane could further promote the expression of osteogenic-related factors. Then, the localization of BMP2, RUNX2, ALP and OPN in cells were determined by CLSM (FIG. 4D). It could be seen that the red fluorescence of M-pSIS and H-pSIS was significantly higher than that of SIS, and H-pSIS expressed the most fluorescent signals, which also confirmed the above trend. The proteins were distributed in cytoplasm far away from the cell membrane. The above results indicated that JH8194 had a certain osteogenic function.

Example 6: Effects of pSIS on OECs Migration and Possible Signal Pathway

It should be noted that the pSIS in Example 6 corresponded to the pSIS-1 in Example 1.

Detection method for the healing-promoting ability of pSIS in vivo was as follows:

The SD rats were anesthetized by inhaling isoflurane and fixed in prone position. After removing the hair of the back, four symmetrical round marks were made by using a punch (2 cm in diameter) on both sides of the spine. Along the round marks, the entire skin was cut off with a scalpel and divided into groups as follows: blank control, SIS membrane group, Bio-Gide membrane group and H-pSIS membrane group, and the membrane was sutured and fixed with subcutaneous tissue. Each rat was raised separately to avoid biting each other. Specific methods of H&E, Masson's trichrome staining and immunohistochemistry were the same as above. The expressions of ITG-β1 and ITG-α3 were detected by immunohistochemistry.

Figure 5A:
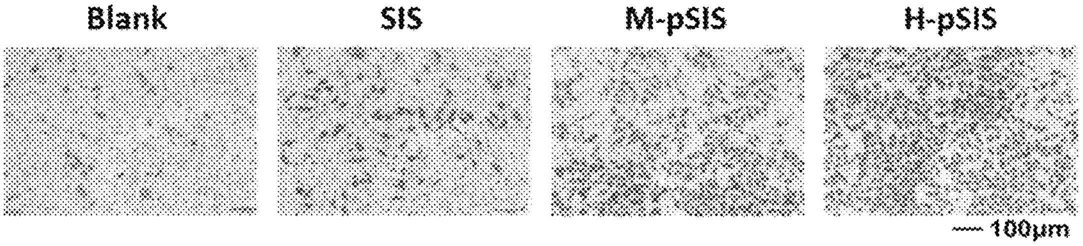
FIG. 5A shows the results of capability of cell migration detected by Transwell experiments.
Figure 5B:
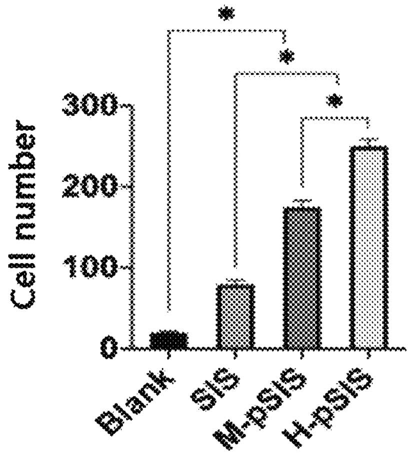
FIG. 5B shows the results of analysis of migrating cells (* represents $p<0.05$).
Figure 5C:
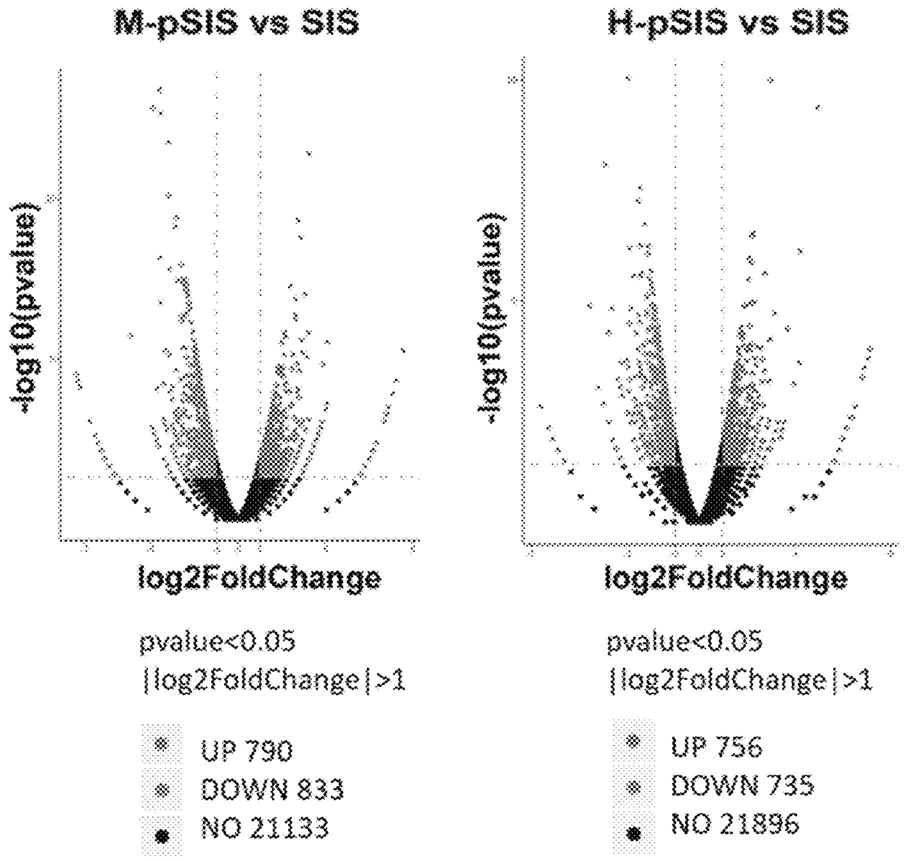
FIG. 5C shows the results of differentially expressed genes screened by RNA-seq.
Figure 5D:
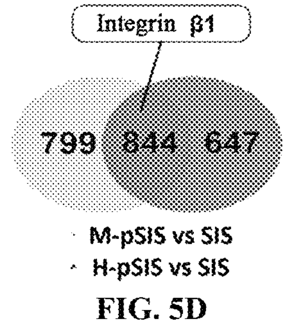
FIG. 5D shows Venn diagram of different genes.
Figure 5E:
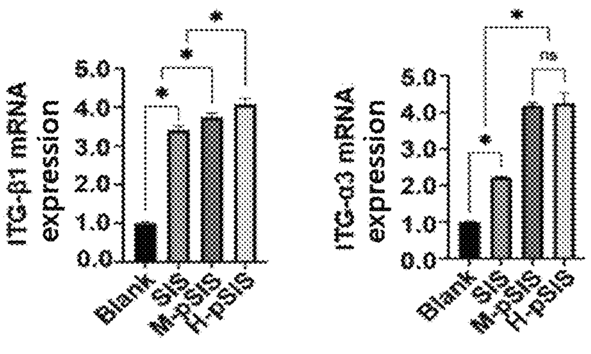
FIG. 5E shows the results of qPCR analysis of migration-related genes.
Figure 5F:
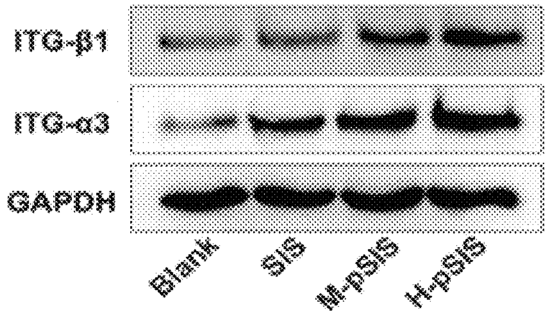
FIG. 5F shows the results of Western Blot analysis of migration-related proteins.
Figure 5G:
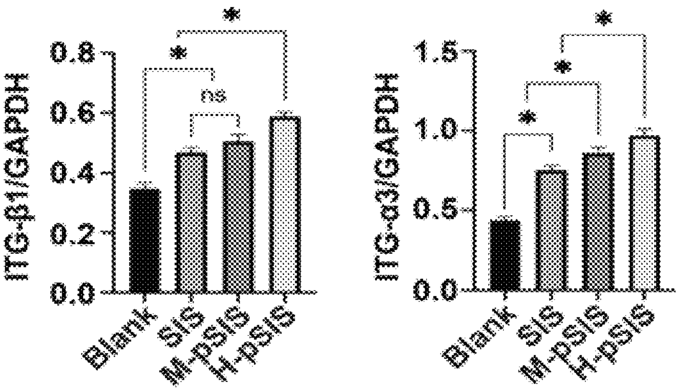
FIG. 5G shows the results of quantitative analysis of Western Blot analysis (* represents $p<0.05$).
Figure 5H:
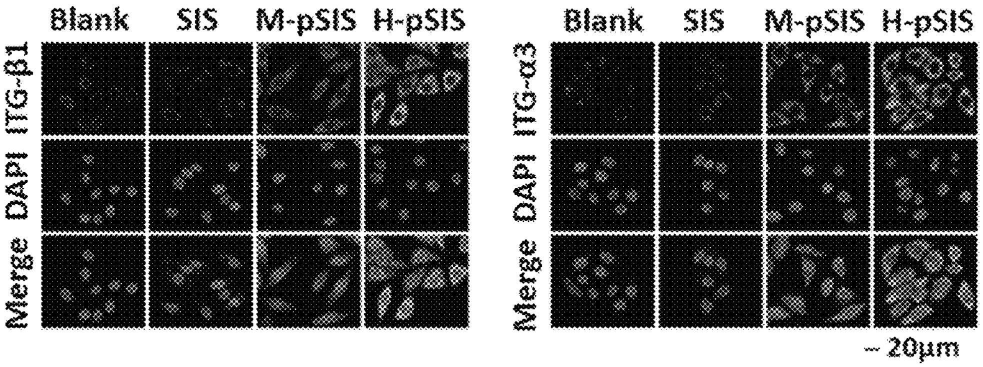
FIG. 5H shows the results of immunofluorescence analysis of migration-related proteins localizations in OECs (ITG-α3, ITG-β1, and nucleus).

FIG. 5A shows the results of capability of cell migration detected by Transwell experiments. FIG. 5B shows the results of analysis of migrating cells (* represents $p<0.05$). FIG. 5C shows the results of differentially expressed genes screened by RNA-seq. FIG. 5D shows Venn diagram of different genes. FIG. 5E shows the results of qPCR analysis of migration-related genes. FIG. 5F shows the results of Western Blot analysis of migration-related proteins. FIG. 5G shows the results of quantitative analysis of Western Blot analysis (* represents $p<0.05$). FIG. 5H shows the results of immunofluorescence analysis of migration-related proteins localizations in OECs (ITG-α3, ITG-β1, and nucleus).

Wound healing process in GBR involved cell proliferation and migration, wound contraction and angiogenesis, collagen deposition and remodeling. Cell migration composed of multi-step processes was necessary for wound repair. Sequence "SHREFPFYGDYGS" of Hst1 contained the minimal elements necessary to promote cell migration, which could promote the migration of oral keratinocytes, oral epithelial cells and gingival fibroblasts. The effect of pSIS on migration of OECs was detected by Transwell experiments (FIG. 5A and FIG. 5B). SIS and pSIS could promote the migration of OECs in which H-pSIS had the strongest ability, suggesting that the chimeric peptide-modified SIS membrane could promote cell migration furtherly and might contribute to the healing of soft tissue.

Subsequently, in order to explore the specific mechanism of chimeric peptides promoting OECs migration, RNA-seq, a novel high-throughput sequencing method, was used to analyze the differentially expressed genes of OECs cultured on SIS, M-PSIS and H-pSIS for 24 h (FIG. 5C). Compared with the SIS group, there were 790 genes increased and 833 genes decreased in M-pSIS group, 756 genes increased and 735 genes decreased in H-pSIS group. Venn diagram showed that 844 genes had identical tendency. After clustering analysis of the different genes, ITG-β1 was found to be related to cell migration (FIG. 5D).

However, most integrin were heterodimeric molecules formed by the subunits a and β in a non-covalent connection, which mediated adhesion and migration of cells and played an essential role in wound repair. Integrin α3β1 was closely related to cell migration and wound healing. It could promote re-epithelialization by accelerating migration of keratinocytes to assist the healing of epithelial wounds. In the GBR region, integrin α3β1 could bind to unprocessed laminin-5, then mediating the migration of connected epithelial cells. Therefore, the expression of ITG-α3 and ITG-β1 of OECs was detected. The expression of ITG-α3 and ITG-β1 in H-pSIS group was higher than that in SIS group (FIGS. 5E to 5G), showing that chimeric peptides could promote the expression of migration-related factors. Then, the localization of ITG-α3 and ITG-β1 in the cells were determined by CLSM (FIG. 5H). It could be seen that the fluorescence in H-pSIS group was stronger than that in SIS group, and the proteins were distributed in cytoplasm far away from cell membrane.

Example 7: Evaluation of Osteogenic Ability of pSIS In Vivo

It should be noted that the pSIS in Example 7 corresponded to the pSIS-1 in Example 1.

Figure 6A:
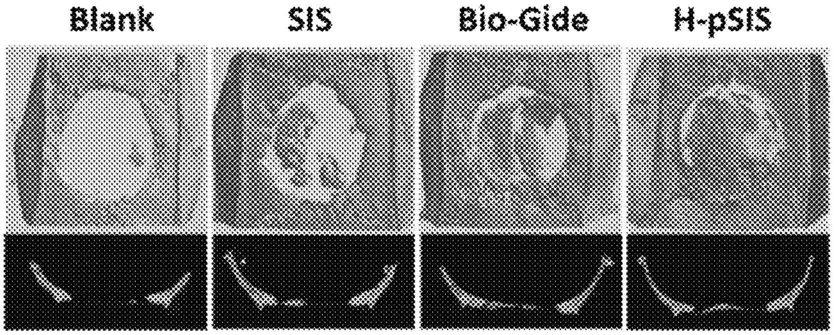
FIG. 6A shows the three-dimensional reconstruction and sagittal images of bone defects covered with SIS, Bio-Gide, and H-pSIS membranes.
Figure 6B:
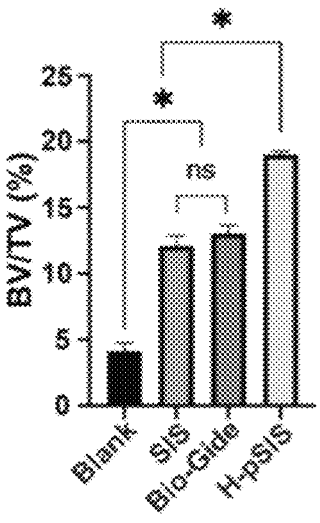
FIG. 6B shows the results of BV/TV of bone defects in different groups (* represents $p<0.05$).
Figure 6C:
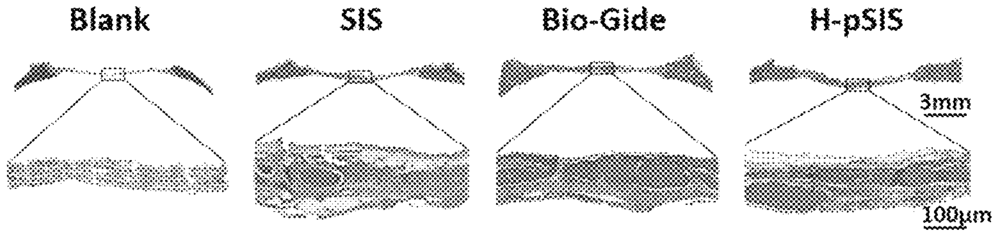
FIG. 6C shows the H&E staining results.
Figure 6D:
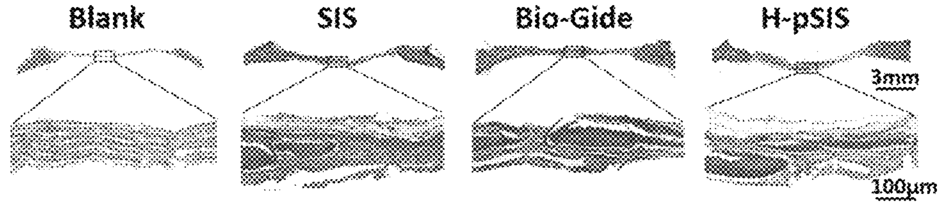
FIG. 6D shows the Masson's trichrome staining results.
Figure 6E:
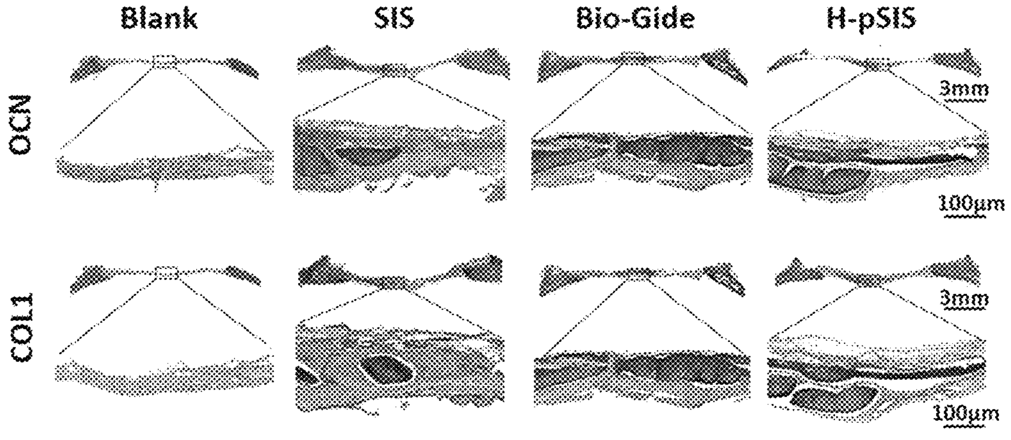
FIG. 6E shows the results of immunohistochemical analysis of OCN and COL1 expression.

FIG. 6A shows the three-dimensional reconstruction and sagittal images of bone defects covered with SIS, Bio-Gide, and H-pSIS membranes. FIG. 6B shows the results of BV/TV of bone defects in different groups (* represents $p<0.05$). FIG. 6C shows the H&E staining results. FIG. 6D shows the Masson's trichrome staining results. FIG. 6E shows the results of immunohistochemical analysis of OCN and COL1 expression.

In animal experiments, the H-pSIS membrane with the best effect was selected for further in vivo study (FIG. 6A to FIG. 6E). The critical size defect (CSD) model of 8 mm round defect which could not be self-healed was made in the rat to evaluate bone regeneration. Moreover, Bio-Gide membrane (commercially available), developed particularly for improving the ossification of bone defects of any origin in GBR, was used as a control. As shown in FIG. 6A, the micro-computed tomography (CT) images of all groups showed that the formation of new bone developed from the defect edge to the center. Twelve weeks after surgery, BV/TV of SIS group and Bio-Gide group were higher than blank control, but there was no significant difference between SIS and Bio-Gide. Moreover, H-pSIS group demonstrated greatly improved osteogenesis in vivo (FIG. 6A and FIG. 6B).

Histological analysis was carried out by hematoxylin-eosin (H&E) and Masson's trichrome staining to evaluate growth of collagen and new bone tissue as well as the infiltration of lymphocytes. Collagen was an important component of bone. Osteoblast-secreted ECM including type I collagen might transform from amorphous and non-crystalline initially to more crystalline gradually leading to promote osteogenesis. In addition, mineralization was a major process for osteoblasts to promote bone formation. Collagen served as a template and might also initiate and propagate mineralization. Therefore, collagen content was closely related to bone formation. As shown in FIG. 6C and FIG. 6D, the defect area of blank control was mainly composed of fibrous tissue with less collagen, and there were no obvious signs of new bone formation. However, the bone defect areas of SIS group, Bio-Gide group and H-pSIS group were rich in collagen and new bone was formed around the stump with small numbers of even none fibrous connective tissue invasion. Meanwhile, the lymphocyte infiltration of all groups was low, indicating that there was no inflammatory reaction (FIG. 6C). The expression of osteocalcin (OCN) and collagen type I (COL1) was detected by immunohistochemistry (FIG. 6E). Twelve weeks after surgery, the control group did not have obvious OCN and COL1 staining while they were highly expressed in the SIS, Bio-Gide and H-pSIS groups, and the H-pSIS group was the highest.

The above results showed that H-pSIS could effectively prevent the fibrous connective tissue from growing into the defect area, providing space for bone formation. The excellent bone regeneration capability of pSIS was helpful to solve the problems of alveolar bone loss caused by periodontitis or tooth loss and insufficient bone mass in the dental implant area. In addition, its unique anti-infective capability conduced to repair infectious bone defects with resisting and preventing tissue inflammation and infection, which was expected to solve the clinical difficulty in repairing bone defects associated with infection.

Example 8: Evaluation of Healing-Promoting Ability of pSIS In Vivo

It should be noted that the pSIS in Example 8 corresponded to the pSIS-1 in Example 1.

Figure 7A:
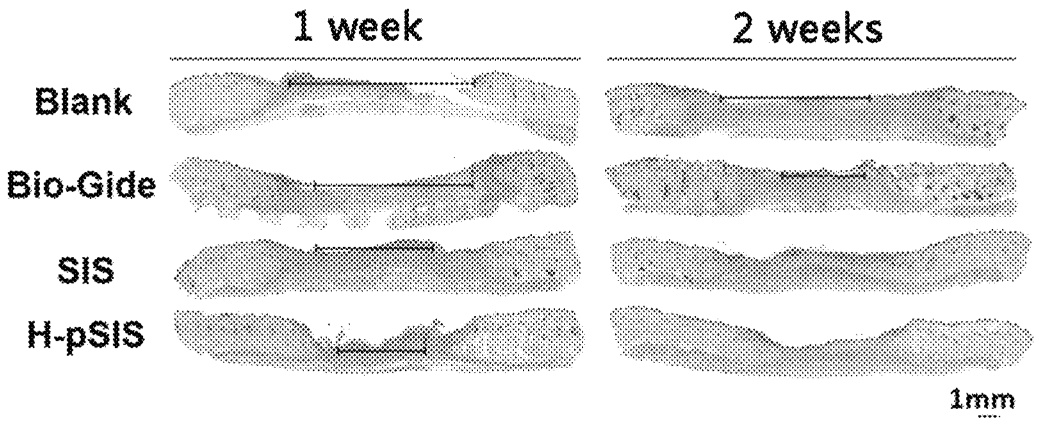
FIG. 7A shows the H&E staining results (segment: length of unepithelized wound).
Figure 7B:
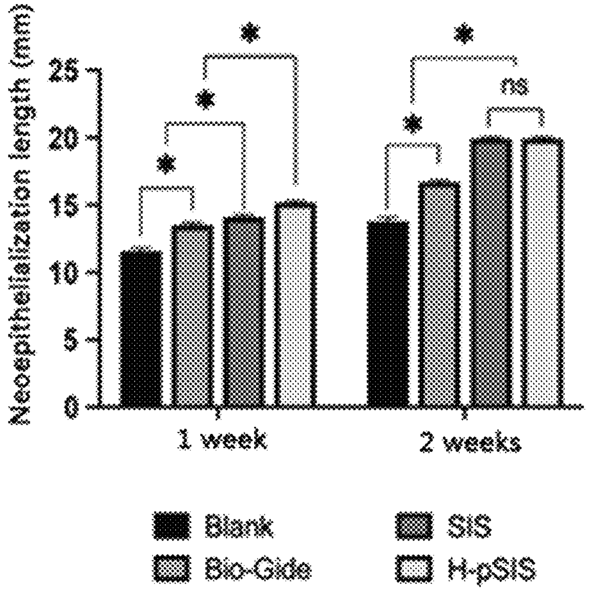
FIG. 7B shows the neoepithelialization length (* represents $p<0.05$).
Figure 7C:
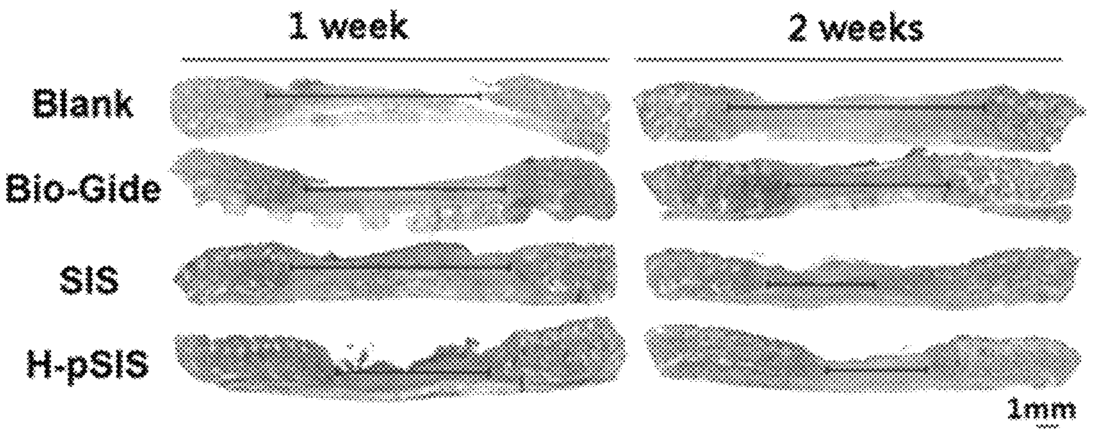
FIG. 7C shows the Masson's trichrome staining results (segment: length of non-collagenous fiber of wound).
Figure 7D:
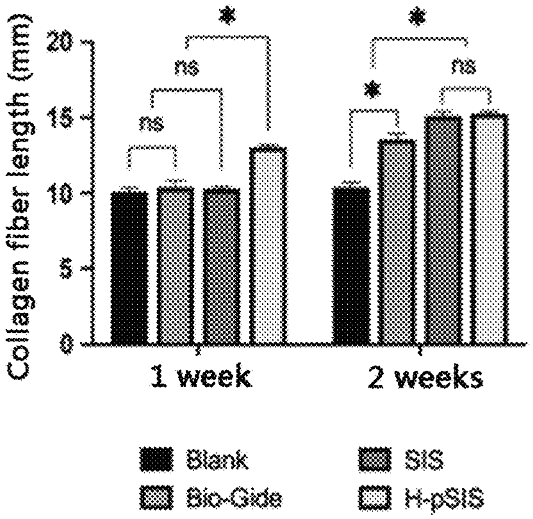
FIG. 7D shows the length of collagen fibers (* represents $p<0.05$).
Figure 7E:
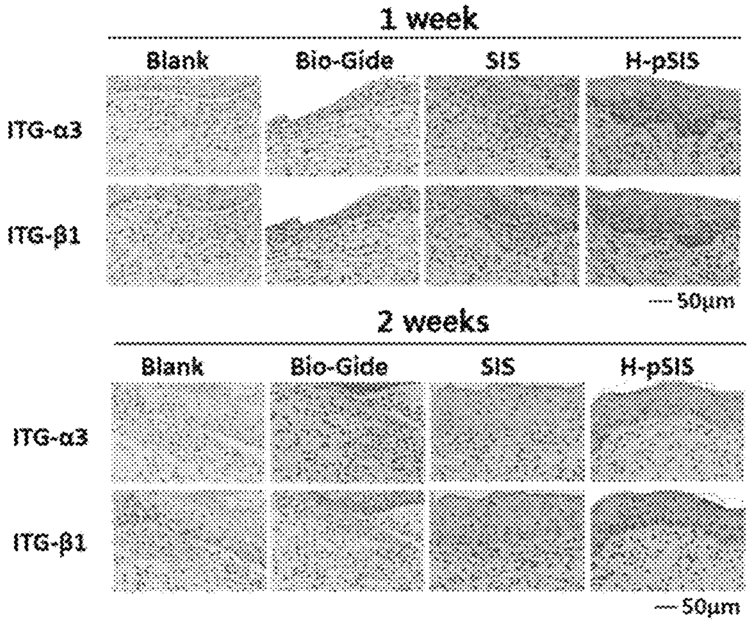
FIG. 7E shows the results of immunohistochemical analysis of ITG-α3 and ITG-β1 expression.

FIG. 7A shows the H&E staining results (segment: length of unepithelized wound). FIG. 7B shows the neoepithelialization length (* represents $p<0.05$). FIG. 7C shows the Masson's trichrome staining results (segment: length of non-collagenous fiber of wound). FIG. 7D shows the length of collagen fibers (* represents $p<0.05$). FIG. 7E shows the results of immunohistochemical analysis of ITG-$\alpha$3 and ITG-$\beta$1 expression.

In order to evaluate the re-epithelialization and collagen content in the soft tissue defect area, histological analysis was carried out by H&E and Masson's trichrome staining (FIG. 7A to FIG. 7D). As shown in FIG. 7A and FIG. 7B, 1 and 2 weeks after surgery of experimental rats, the degrees of re-epithelialization of SIS group and H-pSIS group were significantly higher than those in Bio-Gide and blank control, and the H-pSIS was the highest. Re-epithelialization was a basic feature of wound healing, which was related to the directional migration of keratinocytes. The pSIS membrane might accelerate the re-epithelialization through the promotion of cell migration, which was helpful for the rapid healing of wound. As with bone formation, the successful healing of wounds required the local synthesis of a large amount of collagen, and the collagen content in the soft tissue defect area of H-pSIS was significantly higher than other groups (FIG. 7C and FIG. 7D). It showed that H-pSIS had better ability of promoting soft tissue healing. The expression of ITG-$\alpha$3 and ITG-$\beta$1 was detected by immunohistochemistry, and the positive area was described in FIG. 7E. The levels of ITG-$\alpha$3 and ITG-$\beta$1 in the SIS, Bio-Gide and H-pSIS groups were higher than those in control group, and the H-pSIS group was the highest.

Figure 8:
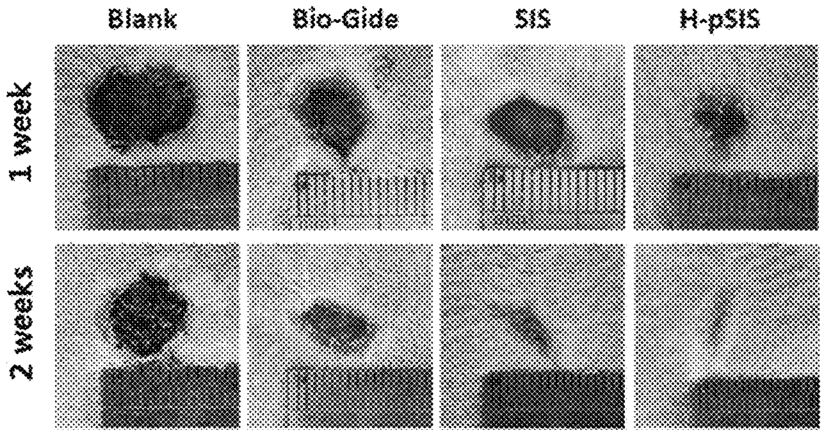
FIG. 8 shows the healing results after 1 and 2 weeks following the operation in the rat experiment.

Meanwhile, the above healing results following 1 and 2 weeks after surgery in the rat experiment were as shown in FIG. 8, finding that the H-pSIS group exhibited a better healing effect.

These results suggested that the chimeric peptide-modified SIS membrane promoted epithelial cell migration and collagen deposition, which might be related to the increased expression of ITG-$\alpha$3 and ITG-$\beta$1.

Example 9: Comparisons of Osteogenic Effects, Inflammation Inhibitory Effects, and Healing Effects of Different Chimeric Peptides-Modified SIS Membranes According to the methods described in Examples 5 to 8 of the present disclosure, the osteogenic effects, inflammation inhibitory effects, and healing effects of the SIS membranes modified with different chimeric peptides (P1 to P8 and P13 to P16) synthesized in the present disclosure were compared.

Figure 9:
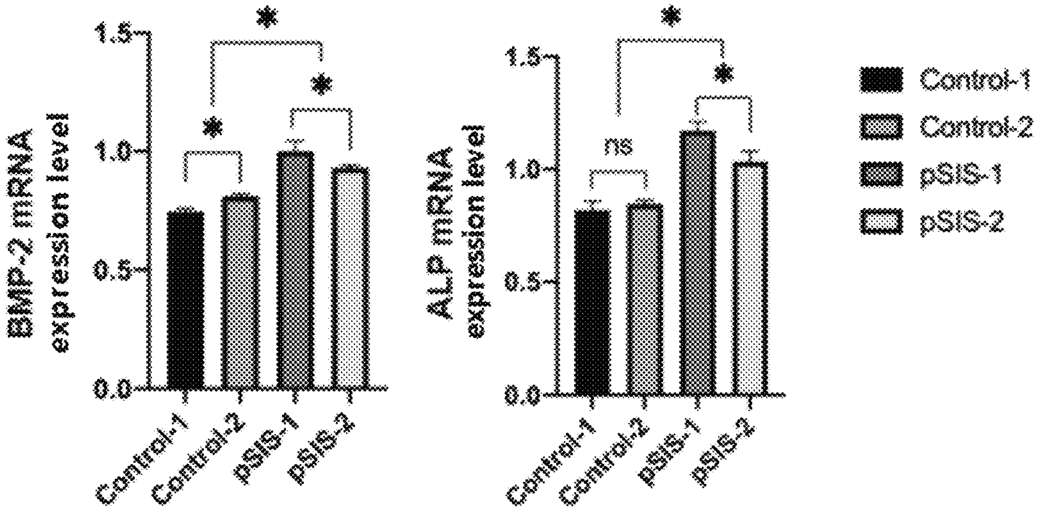
FIG. 9 shows the comparison of osteogenic effects of different chimeric peptides-modified SIS membranes.
Figure 10:
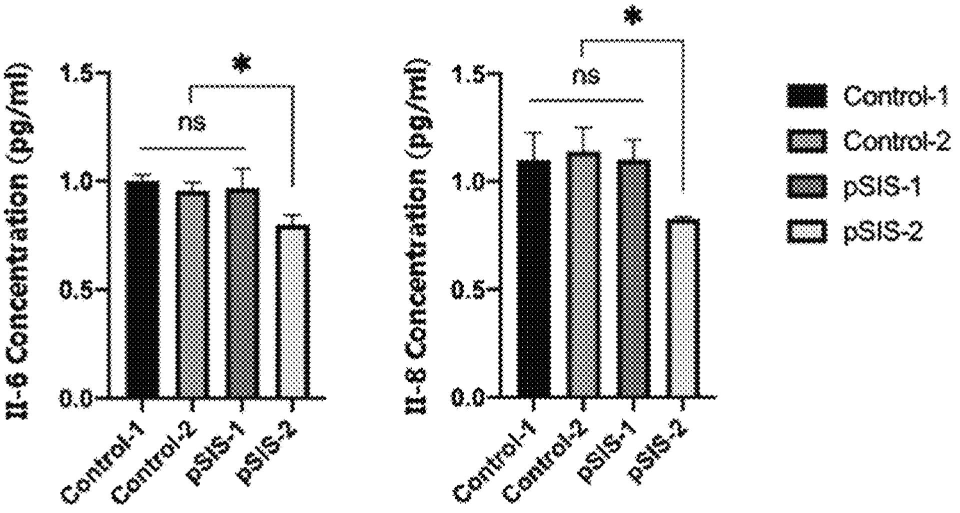
FIG. 10 shows the comparison of inflammation inhibitory effects of different chimeric peptides-modified SIS membranes.
Figure 11:
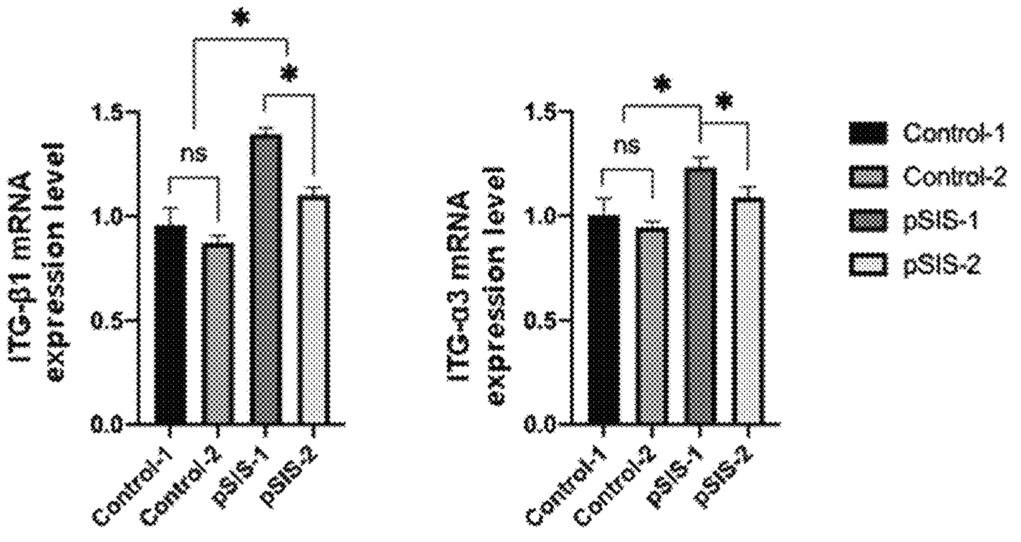
FIG. 11 shows the comparison of healing effects of different chimeric peptides-modified SIS membranes.

The comparison results of the osteogenic effects were as shown in FIG. 9; the comparison results of the inflammation inhibitory effects were as shown in FIG. 10; and the comparison results of the healing effects were as shown in FIG. 11.

In FIG. 9 to FIG. 11, Control-1 was mixing of chimeric peptides shown by P1 to P4; Control-2 was mixing of chimeric peptides shown by P5 to P8; pSIS-1 was mixing of chimeric peptides shown by P9 to P12; and pSIS-2 was mixing of chimeric peptides shown by P13 to P16.

As was clear from the experimental results of FIG. 9 to FIG. 11, pSIS-1 exhibited better osteogenic effects, inflammation inhibitory effects, and healing effects.

Briefly, promoting early healing of wounds after GBR is an effective method to prevent microbial infections and biomaterial exposure complications. At present, some GBR membranes possess a certain role in guiding soft tissue healing, but have single performance and limited effects. The chimeric peptide-modified SIS membrane developed in the present disclosure may simultaneously exert the antibacterial effect and promote soft tissue healing and bone regeneration, which enriches the performance of GBR membrane greatly. The present disclosure has demonstrated that the chimeric peptide-modified SIS membrane (i.e. GBR membrane) is useful for the clinical treatment of infectious bone defects.

The above examples of the present disclosure are provided only for clear illustration of the present disclosure, instead of limiting the embodiments provided herein. For those of ordinary skill in the art, other different forms of variations or alternations may be further made on the basis of the above illustration. Here it is not necessary to exhaust all embodiments, nor is it possible. Any modifications, equivalent substitutions, improvements, etc. made within the spirit and principles of the present disclosure shall be encompassed within the scope of protection for the claims of the present disclosure.

What is claimed is:

1. A chimeric peptide-modified SIS membrane, wherein the sequence of the chimeric peptide comprises at least one sequence in a group consisting of sequences shown as follows:

(i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

2. The chimeric peptide-modified SIS membrane according to claim 1, wherein the sequence of the chimeric peptide consists of at least one sequence in a group consisting of the following sequences: (i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

3. The chimeric peptide-modified SIS membrane according to claim 1, wherein a method for the modification comprises the following steps:

(a) dissolving the chimeric peptide into a solvent to obtain a solution containing the chimeric peptide;

(b) applying the solution obtained in step (a) to the surface of the SIS membrane; and (c) drying the SIS membrane with the solution on the surface thereof.

4. The chimeric peptide-modified SIS membrane according to claim 1, wherein a method for preparing the SIS membrane comprises the following steps:

(i) subjecting a small intestinal submucosa material to primary treatment; and (ii) subjecting the small intestinal submucosa material obtained in step (i) to immunogen removal treatment.

5. The chimeric peptide-modified SIS membrane according to claim 4, wherein the method for preparing the SIS membrane further comprises the following steps:

(iii) laminating the small intestinal submucosa material obtained in step (ii); and (iv) subjecting the laminated small intestinal submucosa material to drying treatment.

6. A method for preparing a chimeric peptide-modified SIS membrane, wherein the method comprises the following steps:

(a) dissolving the chimeric peptide into a solvent to obtain a solution containing the chimeric peptide;

(b) applying the solution obtained in step (a) to the surface of the SIS membrane; and (c) drying the SIS membrane with the solution on the surface thereof to obtain the chimeric peptide-modified SIS membrane;

wherein the sequence of the chimeric peptide comprises or consists of at least one in a group consisting of sequences shown as follow:

(i) a group consisting of a sequence as set forth in SEQ ID NO: 9, a sequence as set forth in SEQ ID NO: 10, a sequence as set forth in SEQ ID NO: 11, and a sequence as set forth in SEQ ID NO: 12; and (ii) a sequence with a conservative substitution as compared to the sequence set forth in (i).

7. The preparation method for the chimeric peptide-modified SIS membrane according to claim 6, wherein a method for preparing the SIS membrane comprises the following steps:

(i) subjecting a small intestinal submucosa material to primary treatment; and (ii) subjecting the small intestinal submucosa material obtained in step (i) to immunogen removal treatment.

8. The preparation method for the chimeric peptide-modified SIS membrane according to claim 7, wherein the method for preparing the SIS membrane further comprises the following steps:

(iii) laminating the small intestinal submucosa material obtained in step (ii); and (iv) subjecting the laminated small intestinal submucosa material to drying treatment.

9. A method for preparing an antibacterial biomaterial, wherein the method comprises utilizing the chimeric peptide-modified SIS membrane according to claim 1.

10. A method for treating an infectious bone defect, wherein the method comprises a step of administering, to a subject, the chimeric peptide-modified SIS membrane according to claim 1.

11. The chimeric peptide-modified SIS membrane according to claim 3, wherein in step (b), soaking the SIS membrane in the solution obtained in step (a).

12. The chimeric peptide-modified SIS membrane according to claim 6, wherein in step (b), soaking the SIS membrane in the solution obtained in step (a).

13. A method for preparing an osteogenic biomaterial, wherein the method comprises utilizing the chimeric peptide-modified SIS membrane according to claim 1.

14. A method for preparing a healing-promoting biomaterial, wherein the method comprises utilizing the chimeric peptide-modified SIS membrane according to claim 1.

15. A method for preparing a biomaterial for treating an infectious bone defect, wherein the method comprises utilizing the chimeric peptide-modified SIS membrane according to claim 1.

* * * * *